US010316103B1

(12) United States Patent
Qi et al.

(10) Patent No.: US 10,316,103 B1
(45) Date of Patent: *Jun. 11, 2019

(54) SYSTEMS AND METHODS FOR ANTI-UROPLAKIN III ANTIBODIES

(71) Applicant: Biocare Medical, LLC, Concord, CA (US)

(72) Inventors: Weimin Qi, Martinez, CA (US); David Tacha, San Ramon, CA (US)

(73) Assignee: Biocare Medical, LLC, Pacheco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/830,473

(22) Filed: Mar. 14, 2013

Related U.S. Application Data

(60) Provisional application No. 61/727,559, filed on Nov. 16, 2012, provisional application No. 61/618,279, filed on Mar. 30, 2012.

(51) Int. Cl.
*C07K 16/30* (2006.01)
*C07K 16/28* (2006.01)
*G01N 33/68* (2006.01)
*G01N 33/532* (2006.01)

(52) U.S. Cl.
CPC ......... *C07K 16/30* (2013.01); *G01N 33/6893* (2013.01)

(58) Field of Classification Search
None
See application file for complete search history.

(56) References Cited

U.S. PATENT DOCUMENTS

| | | | |
|---|---|---|---|
| 4,145,406 A | 3/1979 | Schick et al. |
| 4,254,082 A | 3/1981 | Schick et al. |
| 4,637,996 A | 1/1987 | Konishi |
| 4,687,732 A | 8/1987 | Ward et al. |
| 4,690,890 A | 9/1987 | Loor et al. |
| 4,792,521 A | 12/1988 | Shochat |
| 4,863,875 A | 9/1989 | Bailey et al. |
| 5,089,423 A | 2/1992 | Diamandis et al. |
| 5,108,896 A | 4/1992 | Philo et al. |
| 5,252,487 A | 10/1993 | Bacus et al. |
| 5,280,108 A | 1/1994 | Fanning |
| 5,482,698 A | 1/1996 | Griffiths |
| 5,487,975 A | 1/1996 | Miller et al. |
| 5,565,332 A | 10/1996 | Hoogenboom et al. |
| 5,620,845 A | 4/1997 | Gould et al. |
| 5,691,154 A | 11/1997 | Callstrom et al. |
| 5,719,063 A | 2/1998 | Block |
| 5,869,274 A | 2/1999 | Tsao et al. |
| 5,891,658 A | 4/1999 | Klainer et al. |
| 6,008,057 A | 12/1999 | Glass et al. |
| 6,051,693 A | 4/2000 | Handley et al. |
| 6,252,053 B1 | 6/2001 | Ohbayashi et al. |
| 6,403,769 B1 | 6/2002 | Larochelle et al. |
| 6,409,990 B1 | 6/2002 | Vera |
| 6,476,206 B1 | 11/2002 | Sidransky et al. |
| 6,537,745 B2 | 3/2003 | Chien et al. |
| 6,580,056 B1 | 6/2003 | Tacha |
| 6,723,506 B2 | 4/2004 | Fletcher et al. |
| 6,946,256 B1 | 9/2005 | McKeon et al. |
| 7,354,564 B2 | 4/2008 | Reed |
| 7,354,584 B2 * | 4/2008 | Reed .................... C07K 16/244 424/133.1 |
| 7,422,739 B2 | 9/2008 | Anderson et al. |
| 7,468,425 B2 | 12/2008 | Sidransky et al. |
| 7,674,605 B2 | 3/2010 | Lin et al. |
| 7,785,803 B2 | 8/2010 | Achen et al. |
| 7,846,726 B2 | 12/2010 | Li et al. |
| 7,846,762 B2 | 12/2010 | Rana et al. |
| 7,875,705 B2 | 1/2011 | Iwaneri et al. |
| 7,935,794 B2 | 5/2011 | Pullen |
| 7,935,795 B2 | 5/2011 | Nakajima |
| 7,935,796 B2 | 5/2011 | Lee et al. |
| 7,973,138 B2 | 7/2011 | Liang et al. |
| 8,153,126 B2 | 4/2012 | Violette et al. |
| 8,168,409 B2 | 5/2012 | Calzone et al. |
| 8,338,576 B2 | 12/2012 | Paralkar et al. |
| 8,603,765 B2 | 12/2013 | Tacha |
| 8,852,592 B2 | 10/2014 | Qi et al. |
| 9,005,612 B2 | 4/2015 | Ledbetter et al. |
| 9,156,915 B2 | 10/2015 | Waldman et al. |
| 9,417,243 B2 | 8/2016 | Qi et al. |
| 9,428,576 B2 | 8/2016 | Tacha et al. |
| 9,429,577 B2 | 8/2016 | Qi et al. |
| 9,442,049 B2 | 9/2016 | Barker et al. |
| 9,708,395 B2 | 7/2017 | Tacha |
| 9,816,997 B2 | 11/2017 | Tacha |
| 9,823,251 B2 | 11/2017 | Qi et al. |

(Continued)

FOREIGN PATENT DOCUMENTS

| | | |
|---|---|---|
| EP | 2402370 A1 | 1/2012 |
| EP | 1733437 B1 | 9/2014 |

(Continued)

OTHER PUBLICATIONS

Paul, Fundamental Immunology, 3rd Edition, 1993, pp. 292-295.*
Rudikoff et al. (Proceedings of the National Academy of Sciences USA, vol. 79, p. 1979, 1982).*
Panka et Al. (Proceedings of the National Academy of Sciences USA, vol. 85, 1988).*
Harris et Al. (Biotechnology, vol. 11, p. 1293-1297, 1993).*
Okazaki (The Journal of Experimental Medicine, vol. 202, No. 12, p. 1643-1648, 2005).*
Brown, H. M. Et al. Uroplakin-III to Distinguish Primary Vulvar Paget Disease From Paget Disease Secondary to Urothelial Carcinoma, Human Path. 2002;33:545-548.
Koga, F. et al. Impaired p63 Expression Associates with Poor Prognosis and Uroplakin III Expression in Invasive Urothelial Carcinoma of the Bladder, Clin Cancer Res. 2003;9:5501-5507.

(Continued)

*Primary Examiner* — Michael Allen

(74) *Attorney, Agent, or Firm* — Santangelo Law Offices, P.C.

(57) ABSTRACT

The present invention is related to the anti-Uroplakin III antibodies, kits, cocktails, and use of anti-Uroplakin III antibodies for detection of cancer.

4 Claims, 26 Drawing Sheets

Specification includes a Sequence Listing.

(56) References Cited

U.S. PATENT DOCUMENTS

| | | | |
|---|---|---|---|
| 2002/0094547 A1* | 7/2002 | Burstein | C01N 33/57423 435/7.23 |
| 2002/0106685 A1 | 8/2002 | Henning et al. | |
| 2002/0173053 A1 | 11/2002 | Damaj et al. | |
| 2003/0017491 A1 | 1/2003 | Shi et al. | |
| 2005/0083802 A1 | 4/2005 | Akahoshi et al. | |
| 2005/0186642 A1 | 8/2005 | Tacha | |
| 2006/0148063 A1 | 6/2006 | Fauzzi et al. | |
| 2007/0015908 A1 | 1/2007 | Fischer et al. | |
| 2007/0041972 A1 | 2/2007 | Rother et al. | |
| 2008/0267988 A1 | 10/2008 | Calenoff | |
| 2009/0000360 A1* | 1/2009 | Ogawa | C01N 33/54373 73/61.61 |
| 2009/0191190 A1 | 7/2009 | Barghorn et al. | |
| 2010/0004782 A1 | 2/2010 | Tacha | |
| 2010/0047825 A1 | 2/2010 | Tacha | |
| 2010/0092457 A1 | 4/2010 | Aburatani et al. | |
| 2012/0082999 A1 | 4/2012 | Liao et al. | |
| 2012/0245051 A1 | 9/2012 | Rimm et al. | |
| 2012/0154983 A1 | 11/2012 | Qi et al. | |
| 2012/0321557 A1 | 12/2012 | Kimura | |
| 2014/0004542 A1 | 1/2014 | Qi et al. | |
| 2014/0057803 A1 | 2/2014 | Tacha | |
| 2015/0056635 A1 | 2/2015 | Qi et al. | |
| 2015/0152180 A1 | 6/2015 | Davis et al. | |
| 2016/0009795 A1 | 1/2016 | Tacha et al. | |
| 2016/0216269 A1 | 7/2016 | Tacha et al. | |
| 2016/0333085 A1 | 11/2016 | Tacha et al. | |
| 2016/0334407 A1 | 11/2016 | Qi et al. | |
| 2016/0370370 A1 | 12/2016 | Qi et al. | |
| 2018/0074065 A1 | 3/2018 | Tacha | |

FOREIGN PATENT DOCUMENTS

| | | |
|---|---|---|
| EP | 2900265 B1 | 5/2018 |
| WO | 99/50287 A2 | 10/1999 |
| WO | 2003003906 A2 | 1/2003 |
| WO | 2005054860 A1 | 6/2005 |
| WO | 2010017070 A1 | 2/2010 |
| WO | 2010022736 A2 | 3/2010 |
| WO | 2010124689 A1 | 11/2010 |
| WO | 2012031273 A2 | 3/2012 |
| WO | 2012154983 A3 | 11/2012 |
| WO | 2014052672 A1 | 4/2014 |
| WO | 2014100220 A2 | 6/2014 |
| WO | 2014134587 A1 | 9/2014 |
| WO | 2015051320 A2 | 4/2015 |
| WO | 2015051320 A2 | 8/2016 |

OTHER PUBLICATIONS

Logani, S. et al. Immunoprofile of Ovarian Tumors With Putative Transitional Cell (Urothelial) Differentiation Using Novel Urothelial MarkersHistogenetic and Diagnostic Implications, Am J Surg Pathol 2003;27:1434-1441.

Matsumoto, K. et al. Loss Expression of Uroplakin III is Associated with Clinicopathologic Features of Aggressive Bladder Cancer, Urology. 2008;72:444-449.

Mhawech, P. et al. Immunohistochemical Profile of High-Grade Urothelial Bladder Carcinoma and Prostate Adenocarcinoma, Human Path. 2002;33:1136-1140.

Ohtsuka, Y. et al. Loss of uroplakin III expression is associated with a poor prognosis in patients with urothelial carcinoma of the upper urinary tract, BJU International, 2006;97:1322-1326.

Parker, D. C. et. al. Potential Utility of Uroplakin III, Thrombomodulin, High Molecular Weight Cytokeratin, and Cytokeratin 20 in Noninvasive, Invasive, and Metastatic Urothelial (Transitional Cell) Carcinomas, Am J Surg Pathol 2003;27:1-10.

Wu, X. R. et. al. Mammalian Uroplakins, A group of highly conserved urothelial differentiation-related membrane proteins, J Biol Chem. 1994;269:13716-13724.

Moll, R. et al. Uroplakins, Specific Membrane Proteins of Urothelial Umbrella Cells, as Histological Markers of Metastatic Transitional Cell Carcinomas, American Journal of Pathology, vol. 147, No. 5, Nov. 1995.

Kaufmann, O. et al. Uroplakin III Is a Highly Specific and Moderately Sensitive Immunohistochemical Marker for Primary and Metastatic Urothelial Carcinomas, Am J Clin Pathol 2000;113:683-687.

International Application No. PCT/US2012/37367; Filed May 10, 2012; entitled Systems and Methods for Anti-PAX8 Antibodies.

U.S. Appl. No. 61/618,279, filed Mar. 30, 2012; entitled Systems and Methods for Anti-Uroplakin III Antibodies.

U.S. Appl. No. 61/706,312, filed Sep. 27, 2012; entitled Systems and Methods for Anti-Uroplakin II Antibodies.

U.S. Appl. No. 61/727,559, filed Nov. 16, 2012; entitled Anti-Uroplakin III Antibodies Systems and Methods.

Lai, Y., et al. UPK3A: A Promising Novel Urinary Marker for the Detection of Bladder Cancer, Urology 76 (2), 2010.

Li, S. M., et al. Detection of Circulating Uroplakin-Positive Cells in Patients with Transitional Cell Carcinoma of the Bladder, The Journal of Urology, vol. 162, 931-935, Sep. 1999.

Tacha et al. 'A 6-Anitbody Panel for the Classification of Lung Adenocarcinoma Versus Squamous Cell Carcinoma.' Appl Immunohistochem Mol Morphol. 20(3): 201-7, May 2012.

Brown, et al. 'Tissue Preserving Antibody Cocktails to Differentiate Primary Squamous Cell Carcinoma, Adenocarcinoma, and Small Cell Carcinoma of Lung.' Arch Pathol Lab Med. 137(9):1274-81. Jan. 4, 2013.

Whithaus K., et al. Evaluation of Napsin A, Cytokeratin 5/6, p63, and Thyroid Transcription Factor 1 in Adenocarcioma Versus Squamous Cell Carcinoma of Lung. Arch Pathol Lab Med. 2012; 136: 155-162.

Savci-Heijink C. D., et al. The role of desmoglein-3 in the diagnosis of squamous cell carcinoma of the lung. Am J Pathol. 2009;174(5): 1629-1637.

Ring B. Z., et al. A novel five-antibody immunohisto-chemical test for subclassification of lung carcinoma. Mod Pathol. 2009;22(8): 1032-1043.

Mukhopadhyay S., et al. Subclassification of Non-small Cell Lung Carcinomas lacking Morphologic Differentiation on biopsy specimens: Utility of an Immunohistochemical Panel Containing TTF-1, Napsin A, p63 and CK 516. Am J Surg Pathol, 2011; 35(1): 15-25.

Bishop J. A., p40 (ΔNp63) is superior to p63 for the diagnosis of pulmonary squamous cell carcinoma, Modern Pathology (2011), 1-11; republished Mar. 2012;25(3):405-15.

Ikeda S, et al. "Combined immunohistochemistry of beta-catenin, cytokeratin 7, and cytokeratin 20 is useful in discriminating primary lung adenocarcinomas from metastatic colorectal cancer.", BMC Cancer. Feb. 2, 2006;6:31.

Brown, et al. Tissue-Preserving Antibody Cocktails to Differentiate Primary Squamous Cell Carcinoma, Adenocarcinoma, and Small Cell Carcinoma of Lung, Arch Pathol Lab Med, Early Release Online, Jan. 4, 2013.

Jain, et al. Atypical ductal hyperplasia: interobserver and intraobserver variability. Mod. Pathol. (2011) 24, 917-923.

Barbareschi, et al. p63, a p53 homologue, is a selective nuclear marker of myoepithelial cells of the human breast. Am J Surg. Pathol 25(8): 1054-1060, 2001.

Bergholz, et al. 'Role of p63 in development, tumorigenesis and cancer progression'. Cancer Microenvironment (2012) 5:311-322.

Di Como, et al. 'p63 Expression Profiles in Human Normal and Tumor Tissues'. Clinical Cancer Research. vol. 8, 494-501, Feb. 2002.

Hibl, et al. 'AIS is an oncogene amplified in squamous cell carcinoma'. PNAS, May 9, 2000, vol. 97, No. 10, 5462-5467.

Kaghdad, et al. 'Monoallelically Expressed Gene Related to p53 a 1p36, a Region Frequently Deleted in Neuroblastoma and Other Human Cancers'. Cell, vol. 90, 809-819, Aug. 22, 1997.

Karni-Schmidt, et al. Distinct Expression Profiles of p63 Variants during Urothelial Development and Bladder Cancer Progression. Am J Pathol vol. 178, No. 3, Mar. 2011.

Khoury, et al. 'p53 Isoforms: an Intracellular Microprocessor?' Genes & Cancer / vol. 2 No. 4 (2011).

(56) References Cited

OTHER PUBLICATIONS

Murray-Zmijewski, et al. 'p53/p63/p73 isoforms: an orchestra of isoforms to harmonise cell differentiation and response to stress'. Cell Death and Differentiation (2006) 13, 962-972.
Nobre, et al. 'p40: A p63 isoform useful for lung cancer diagnosis—a Review of the Physiological and Pathological Role of p63'. Acta Cytologica 2013; 57:1-8.
Nonaka, 'A study of Np63 expression in lung non-small cell carcinomas'. Am J Surg Pathol vol. 36 No. 6 Jun. 2012.
Nylander, et al. 'Differential expression of p63 isoforms in normal tissues and neoplastic cells'. J Pathol 2002; 198: 417-427.
Osada, et al. 'Cloning and functional analysis of human p51, which structurally and functinoally resembles p53'. 1998 Nature Publishing Group http://www.nature.com/naturemedicine. vol. 4, No. 7, Jul. 1998.
Pelosi, et al. 'Np63 (p40) and Thyroid Transcription Factor-1 Immunoreactivity on small biopsies or cellblocks for typing non-small cell lung cancer'. Journal and Thoracic Oncology, vol. 7, No. 2, Feb. 2012.
Senoo et al. 'A second p53-Related Protein, p73L, with High Homology to p73'. Biochemical and biophysical research communications 248, 603-607 (1998).
Trink, et al. 'A new human p53 homologue'. 1998 Nature Publishing Group http://www.nature.com/naturemedicine. Nature Medicine, vol. 4, No. 7, Jul. 1998.
Signoretti, Sabina 'p63 is a prostate basal cell marker and is required for prostate development'. Am J Pathol, vol. 157, No. 6, Dec. 2000.
Yang, et al. 'p63, a p53 homolog at 3q27-29, encodes multiple products with transactivating, death-inducing, and dominant-negative activities'. Molecular Cell, vol. 2, 305-316, Sep. 1998.
Bowen, et al. 'Emerging roles for PAX8 in ovarian cancer and endosalpingeal development.' Gynecologic Oncology, vol. 104, No. 2, Feb. 2007, 331-337.
Tacha, D. et al. Expression of PAX8 in Normal and Neoplastic Tissues: A Comprehensive Immunohistochemical Study. Appl. Immun. Mol. Morph. 2011.
Kobel M. et al. Ovarian carcinoma subtypes are different diseases: Implications for biomarker studies. PLoS Med. Dec. 2, 2008; 5(12): e232.
Nonaka D. et al. Expression of PAX8 as useful marker in distinguishing ovarian carcinomas from mammary carcinomas. Am J Surg Pathol. Oct. 2008; 32(10):1566-71.
Tong G. X. et al. Expression of PAX8 in nephrogenic adenoma and clear cell adenocarcinoma of the lower urinary tract: evidence of related histogenesis? Am J Surg Pathol. Sep. 2008; 32(9):1380-7.
Tong G. X. et al. Expression of PAX8 in normal and neoplastic renal tissues: an immunohistochemical study. Mod. Pathol. Sep. 2009; 22 (9):1218-27.
Mazal P. R. et al. Expression of aquaporins and PAX-2 compared to CD10 and cytokeratin 7 in renal neoplasms: a tissue microarray study. Mod. Pathol. Apr. 2005; 18(4):535-40.
Avery A. K. et al. Use of antibodies to RCC and CD10 in the differential diagnosis of renal neoplasms. Am J Surg Pathol. Feb. 2000; 24(2):203-10.
Zhou M. et al. The usefulness of immunohistochemical markers in the differential diagnosis of renal neoplasms. Clin Lab Med. Jun. 2005; 25(2):247.
Kuehn A. et al. Expression analysis of kidney-specific cadherin in a wide spectrum of traditional and newly recognized renal epithelial neoplasms: diagnostic and histogenetic implications. Am J Surg Pathol. Oct. 2007; 31(10):1528-33.
Mazal P. R. et al. Expression of kidney-specific cadherin distinguishes chromophobe renal cell carcinoma from renal oncocytoma. Hum Pathol. Jan. 2005; 36(1):22-8.
Zhu W. et al. WT1, monoclonal CEA, TTF1, and CA125 antibodies in the differential diagnosis of lung, breast, and ovarian adenocarcinomas in serous effusions. Diag Cytopathol. Jun. 2007; 35(6):370-5.
Tornos C. et al. Expression of WT1, CA 125, and GCDFP-15 as useful markers in the differential diagnosis of primary ovarian carcinomas versus metastatic breast cancer to the ovary. Am J Surg Pathol. Nov. 2005; 29(11):1482-9.
Lee A. H. et al. The expression of Wilms' tumour-1 and CA125 in invasive micropapillary carcinoma of the breast. Histopathology. Dec. 2007; 51(6):824-8.
Reid-Nicholson M. et al. Immunophenotypic diversity of endometrial adenocarcinomas: implications for differential diagnosis. Mod Pathol. Aug. 2006; 19(8):1091-100.
Zhang P. et al. Immunohistochemical analysis of thyroid-specific transcription factors in thyroid tumors. Pathol Int 2006;56:240-245.
Ozcan A. et al. PAX 8 expression in non-neoplastic tissues, primary tumors, and metastatic tumors: a comprehensive immunohistochemical study. Mod Pathol 2011;24:751-764.
Laury A.R. et al. A comprehensive analysis of PAX8 expression in human epithelial tumors. Am J Surg Pathol 2011;35:816-826.
Moretti L. et al. N-terminal PAX8 polyclonal antibody shows cross-reactivity with N-terminal region of PAX5 and is responsible for reports of PAX8 positivity in malignant lymphomas. Mod Pathol 2011.
Long K. B. et al. PAX8 Expression in well-differentiated pancreatic endocrine tumors: correlation with clinicopathologic features and comparison with gastrointestinal and pulmonary carcinoid tumors. Am J Surg Pathol 2010;34:723-729.
Haynes C. M. et al. PAX8 is expressed in pancreatic well-differentiated neuroendocrine tumors and in extrapancreatic poorly differentiated neuroendocrine carcinomas in fine-needle aspiration biopsy specimens. Cancer Cytopathol 2011;119:193-201.
Sangoi A. R. et al. PAX8 expression reliably distinguishes pancreatic well-differentiated neuroendocrine tumors from ileal and pulmonary well-differentiated neuroendocrine tumors and pancreatic acinar cell carcinoma. Mod Pathol 2011;24:412-424.
Albadine R. et al. PAX8 (+)/p63 (−) immunostaining pattern in renal collecting duct carcinoma (CDC): a useful immunoprofile in the differential diagnosis of CDC versus urothelial carcinoma of upper urinary tract. Am J Surg Pathol 2010;34:965-969.
Laury A.R. et al. PAX8 reliably distinguishes ovarian serous tumors from malignant mesothelioma. Am J Surg Pathol 2010;34:627-635.
Turque N. et al. Pax-QNR/Pax-6, a paired box- and homeobox-containing gene expressed in neurons, is also expressed in pancreatic endocrine cells. Mol Endocrinol 1994;8:929-938.
Wu XR, Kong XP, Pellicer A, Kreibich G, Sun TT.; Uroplakins in urothelial biology, function, and disease; Kidney Int. Jun. 2009;75(11):1153-65.
Wu X, Kakehi Y, Zeng Y, Taoka R, Tsunemori H, Inui M. J ; Uroplakin II as a promising marker for molecular diagnosis of nodal metastases from bladder cancer: comparison with cytokeratin 20.; Urol. Dec. 2005;174(6):2138-4.
Olsburgh J, Harnden P, Weeks R, Smith B, Joyce A, Hall G, Poulsom R, Selby P, Southgate J.J; Uroplakin gene expression in normal human tissues and locally advanced bladder cancer Pathol. Jan. 2003;199(1):41-9.
Lu JJ, Kakehi Y, Takahashi T, Wu XX, Yuasa T, Yoshiki T, Okada Y, Terachi T, Ogawa O; Detection of circulating cancer cells by reverse transcription-polymerase chain reaction for uroplakin II in peripheral blood of patients with urothelial cancer; Clin Cancer Res. Aug. 2000;6(8):3166-71.
Kong XT, Deng FM, Hu P, Liang FX, Zhou G, Auerbach AB, Genieser N, Nelson PK, Robbins ES, Shapiro E, Kachar B, Sun TT.; Roles of uroplakins in plaque formation, umbrella cell enlargement, and urinary tract diseases. J Cell Biol. Dec. 20, 2004;167(6):1195-204.
Okegawa T, Kinjo M, Nutahara K, Higashihara E.; Value of reverse transcription polymerase chain assay in peripheral blood of patients with urothelial cancer. J Urol. Apr. 2004;171(4):1461-6.
Hong-Ying Huang, Shahrokh F. Shariat, *Tung-Tien Sun, Herbert Lepor, Ellen Shapiro, Jer-Tsong Hsieh, Raheela Ashfaq, Yair Lotan, and Xue-Ru Wu, ; Persistent Uroplakin Expression in Advanced Urothelial Carcinomas: Implications in Urothelial Tumor Progression and Clinical Outcome. Hum Pathol. Nov. 2007; 38(11): 1703-1713.
Lorenzo P.I. et al. Immunohistochemical assessment of Pax8 expression during pancreatic islet development and in human neuroendocrine tumors. Histochem Cell Biol 2011;136:595-607.

(56) References Cited

OTHER PUBLICATIONS

Ye J. et al. Diagnostic utility of PAX8, TTF-1 and napsin A for discriminating metastatic carcinoma from primary adenocarcinoma of the lung. Biotech Histochem 2011.

Moll, R. et al. Uroplakins, Specific Membrane Proteins of Urothelial Umbrella Cells, as Histological Markers of Metastatic Transitional Call Carcinomas. Am J Pathol, vol. 147, No. 5, Nov. 1995.

Saeb, Parsy, et al. 'Diagnosis of Bladder Cancer by Immunocytochemical detection of minichromosome maintenance protein-2 in cells retrieved from urine' British Journal of Cancer (2012) 107, 1384-1391.

Chopra, N. et al. 'Inducing Protectice Antibodies Against Ring-Infected Erythrocyte Surface Peptide Antigen of Plasmodium Falciparum Using Immunostimulating Complex (Iscoms) Delivery.' Med Microbiol. Immunol. Nov. 2000 vol. 189, No. 2: pp. 75-83.

Calbiochem-Novabiochem International. P40(Ab-1) Cat# PC373 [datasheet]. USA 2000; 2 pages.

Abcam. Understanding Secondary Antibodies: Fragment Antigen Binding Antibodies and Isotopes. USA 2012; 12 pages.

Biocare Medical. MACH 2 Double-Stain 2 [datasheet]. USA Mar. 2, 2011; 2 pages.

Yamaguchi, K. et al. Circulating Antibodies to P40AIS in the Sera of Respiratory Tract Cancer Patients. Int. J. Cancer. Nov. 20, 2000. vol. 89 No. 6; 5 pages.

Vaidyanathan, P. Aperio-Definins Digital Pathology Solutions [Presentation]. Jul. 7, 2011. Aperio Webinar. <http://www.aperio.com/sites/default/files/events/070611_Spectrum_Plus_ppt_for_webinar_on_integration.pd>; 10 pages.

Tacha, et al. "An Immunohitochemical Analysis of a Newly Developed Mouse Monocloncal p40 (BC28) in Lung, Bladder, Skin, Breast, Prostate, and Head and Neck Cancers" 2014 College of American Pathologists, Early Online Release, Arch Pathol. Lab Med. 8 pages, postes Feb. 2014.

Tockman et al, Consideration in Bringing a Cancer Biomarker to Clinical Application. Cancer Research vol. 52 p. 2711s (1992).

Janicke et al., Urokinase-type Plasminogen Activator (u-PA) Antigen in a Predictor of Early Relapse in Breast Cancer. Fibrinolysis vol. 4 p. 69 (1990).

de Pascalis et al., Grafting of "Abbreviated" Complementarity-Determining Regions Containing Specificity-Determining Residues Essential for Ligand Contact to Engineer a Less Immunogenic Humanized Monoclonal Anitbody. (The Journal of Immunology (2002) 169,3076-3084).

Brown et al. Tolerance to Single, but Not Multiple, Amino Acid Replacements in Anitbody VH CDR2. (J. Immunol. May 1996; 156(9):3285-3291.

Casset et al. A Peptide Mimetic of an Anti-CD4 Monoclonal Antibody by Rational Design. (2003) BBRC 307, 198-205.

Ogawa, K. et al. Immunohistochemical Analysis of Uroplakins, Urothelial Specific Proteins, in Ovarian Brenner Tumors, Normal Tissues, and Benign and Neoplastic Lesions of the Female Genital Tract. Am J Pathol. 1999;155:1047-1050.

Nonaka, D. et al. Diagnostic Utility of Thyroid Transcription factors PAX8 and TTF-2 in Thyroid Epithelial Neoplasms. Mod Pathol. Feb. 2008; 21(2): 192-2004.

GenBank Accession No. CAG30470. SOX10 (*Homo sapiens*). Oct. 16, 2008. (Retrieved from the Internet Dec. 4, 2014: <http://www.ncbi.nlm.nih.gov/protein/CAG30470.1>] 2 pages.

Bondurand, et al. The role of SOX10 during enteric nervous system development. Dev Bioi. Epub May 2, 2013, 382 (1):330-43.

Sanderson, SO et. al., "An Analysis of the p63/α-Methylacyl Coenzyme A Racemase Immunohistochemical Cocktail Stain in Prostate Needs Biopsy Specimens and Tissue Microarrays", Am. J. Clin. Path., 2004; 121:220-225.

Zhou, Ming. al., "Basal Cell Cocktail (34βE12+p63) Improves the Detection of Prostate Basal Cells", Am. J. Surg. Path., 2003: 27(3), 365-371.

Zhou, Ming et al., "Expression and Disgnostic Utility of Alpha-Methylacyl-CoA-Racemase (P504S) in Foamy Gland and Pseudohyperplastic Prostate Cancer", Am. J. Surgical Pathology 27(6): 772-778, 2003.

Anonymous: "PIN cocktail-2 (P504S+p63)", Biocarta. May 4, 2003, pp. 1-2. XP002667408, Retrieved from the Internet: URL:http://www.biocarta.com/TDS/PM205DSH.pdf [retrieved on Jan. 18, 2012].

Anonymous: "Double vision. The double stain, polymer detection system", Biocare Medical, Aug. 2, 2003, pp. 1-3, XP002667409, retrieved from the Internet: URL: htt12 ://web/archive. org/web/20030802112943/httQ :1/biocare. net/Detection. htm [retrieved Jan. 18, 2012].

Anonymous: "Double vision, The double stain, polymer detection system", Biocare Medical, Oct. 2, 2003, pp. 1-3, XP002667410, retrieved from the Internet: URL:htt12 ://web/archive .org/web/20031 002060452/httQ ://biocare. net/Detection. htm [retrieved Jan. 18, 2012).

Anonymous: "Double vision, The double stain, polymer detection system", Biocare Medical, Jan. 1, 2004, pp. 1-5, XP002667411, retrieved from the Internet: URL: htt12 ://web/archive .org/web/20040 1 01180833/httQ :1/biocare. net/Detection. htm [retrieved Jan. 18, 2012].

Susan Van Noorden., "Immunocytochemistry for light microscopy a technical update", The biomedical Scientist, XP-002522654, Aug. 2003, pp. 808-811.

Rami Suzuki. et al., "Proliferation and differentiation in the human breast during pregnancy", Differentiation. vol. 66, No. 2-3, XP-002522647, Oct. 2000, pp. 106-115.

BioGenex datasheet, Rabbit Anti-PIN4 Cocktail—AB448ME, Doc. No. 932-448ME Rev A, release date Aug. 17, 2007.

C.M. van der Loos, "Immunoenzyme Multiple Staining Methods", Microscopy Handbooks 45, (1999).

Hiromichi Tsurui, et al., "Seven-color Fluorescence Imaging of Tissue Samples Based on Fourier Spectroscopy and Singular Value Decomposition", The Journal of Histochemistry & Cytochemistry, vol. 48, No. 5, XP-002522648, May 2000, pp. 653-662.

David Y. Mason, et al., "Double immunofluorescence labelling of routinely processed paraffin sections", Journal of Pathology, vol. 191, No. 4. XP-002522649, Aug. 2000, pp. 452-461.

Susan Van Noorden., "Advances in immunocytochemistry", Folia Histochemica Et Cytobiologica, vol. 40, No. 2, XP-008104795, 2002, pp. 121-124.

Chris M. Van der Loos, et al., "Immunohistochemical Detection of Interferon-y: Fake or Fact?", The Journal of Histochemistry & Cytochemistry, vol. 49, No. 6, XP-002522653, Jun. 2001. pp. 699-709.

Chris M. Van der Loos. et al. "The Animal Research Kit (ARK} Can Be Used in a Multistep Double Staining Method for Human Tissue Specimens", The Journal of Histochemistry & Cytochemistry, vol. 48, (10): 1431-1437 (2000).

C.M. Van der Loos, et al, "Multiple immunoenzyme staining techniques Use of fluoresceinated, biotinylated and unlabeled monoclonal antibodies", Journal of Immunological Methods, 117 (1989), pp. 45-52.

Chris M. Vander Loos. et al. "An Immunoenzyme Triple-staining Method Using Both Polyclonal and Monoclonal antibodies from the same Species. Application of combined direct, Indirect, and Avidin-Biotin Complex (ABC) Technique", The Journal of Histochemistry and Cytochemistry, vol. 35, No. 11, pp. 1199-1204 (1987).

Chris M. Vander Loos, et al. "Practical suggestions for successful immunoenzyme double-staining experiments", Histochemical Journal (25), pp. 1-13 (1993).

Brunangelo Falin!, et al., "Double Labeled-Antigen Method for Demonstration of Intracellular Antigens in Paraffin-embedded Tissues", The Journal of Histochemistry and Cytochemistry. vol. 30, No. 1, pp. 21-26 (1982).

Data Sheet Fast Red Stubsrate Pack and Compponents for Use with Alakline Phosphatase Detection Kits & BioGenex Automated Staining Systems (Doc. No. HK180, Rev. No. F112) Jul. 1, 2003 accessed from web.archive. org/web/20030701115828/http://www.bioQenex.conn/biOQenex h.html.

(56) References Cited

OTHER PUBLICATIONS

Vector Red Alkaline Phosphatase Substrate Kit I Cat. No. SK-5100, Oct. 31, 2000, accessed from web.archive.org/web/20031202200453/ http://www.vector.labs.com/protocols.asp.

Cordell et al, Journal of Histochemistry and Cytochemistry, 1984, vol. 32, No. 2 pp. 219-229 attached online version htte://jhc.sageeub.com/content/32/2/219.

Instructions for Universal Alkaline Phosphatase Immunostaining Kit (for Mouse and Rabbit Primary Antibodies) Cat. #KA-50F Apr. 7, 2003 Accessed from web.archive.org/web/20030407222427/http:I/ dbiosys.com/new/index.asp?fuse=dsp cat&id=5.

Elias, Immunohistopathology—A Practical Approach to Diagnosis, 2nd Ed., American Society for Clinical Pathology Press: Chicago, © 2003, p. 36.

Molinie, V. et. al., Mod. Pathol., 2004, 17, 1180.

Paner, GP, . et. al., Best Prac. In Diag. Immunohist.: Prostate, 2008, 132, 1388.

Rubin, MA et. al., JAMA, 2002,287, 1662.

Shah, RB et. al., Am. J. Surg. Path., 2002, 26, 1161.

Signoretti, Set. al., Am. J. Path., 2000, 157, 1769.

Tacha, DE and Miller, RT, Appl. Immunohistochem. Mol. Morph .. 2004, 12, 75.

Tavora. F and Epstein, JI, Am. J. Surg. Path., 2008, 32, 1060.

Yang, Yet. al., Am. J. Path., 1997, 150, 693.

Abrahams, NA, et. a f., Histopathology, 2002, 41, 35.

Adley, BP et. al., Am. J. Clin. Path., 2006, 126, 849.

Beach, R et. al., Am. J. Surg. Path., 2002, 26, 1588.

Bostwick, DG and Qian, J., Mod. Pathol., 2004, 17, 360.

DAKO Press Release Sep. 14, 2009, New Duoflex Cocktail Antibodies.

DAKO Screen Shot DuoFlex Cocktail, Anti-AMACR, Anti-Cytokeratin HMW, Anti-Cytoderatin 5/6: Oct. 5, 2009.

Herawi, M and Epstein, JI, Am. J. Surg. Path., 2007, 31, 889.

Jiang, Z et. al., Am. J. Clin. Path., 2004, 122, 275.

Jiang, Z et. al., Am. J. Clin. Path., 2005, 123,231.

Jiang, Z et. al., Am. J. Surg. Path., 2001, 25, 1397.

Luo, J et. al., Cancer. Res., 2002, 62, 2220.

Reis-Filho et al, Virchows Arch. (2003) vol. 443, pp. 122-132.

12 pages from catalog: "product information form the Sigma-Aldrich Online Catalog" at sigmaaldrich.com/ .. ./ProductDetail. do?I . . . accessed Feb. 14, 2011.

8 pages from catalog: "product information form the Sigma-Aldrich Online Catalog" at sigmaaldrich.com/.. ./ProductDetail.do?I. . . accessed Feb. 16, 2011.

Epstein, JI, and Netto, GJ., Biopsy interpretation of the prostate, 2008, Lippincott, Williams & Wilkins: Philadelphia, p. 99.

BioSB p40 IHC of p40 on an FFPE Prostate Tissue, http://www.biosb.com/p40-page, Jul. 29, 2015, 4 pages.

Baty et al. 'Gene profiling of Icinical routine biopsies and prefiction of survival in non-small cell lung cancer.' Am J Respir Crit Care Med. 181(2):181-8.15 Oct. 2009.

European Patent App. No. 14178215.1 Examination Report dated Dec. 15, 2015, 5 pages.

European Patent App. No. 14178215.1 Search Report dated Dec. 1, 2014, 11 pages.

Cartron, et al. Therapeutic activity of humanized anti-DC20 monoclonal antibody and polymorphism in IgG Fc receptor gene. www.bloodjournal.org, Jan. 21, 2016. 6 pages.

Creative Biolabs, Chimeric IgG construction; (c) 2007-2016 Creative Biolabs, 2 pages.

Eng, Hui-Yan, et al. Enhanced antigen detection in immunohistochemical staining using a 'digitized' chimeric antibody. Oxford, Protein Engineering, Design & Selection, 2016, vol. 29 No. 1, pp. 11-21. Sep. 25, 2015, 11 pages.

Carter, Paul J. Potent antibody therapeutics by design. Nature Reviews, Immunology. vol. 6, May 2006. pp. 343-357. 15 pages.

Chames et al. Therapeutic antibodies: success, limitations and hopes for the future. Themed Section: Vector Design and Drug Delivery Review. British Journal of Pharmacology (2009) 157,200-233.

Jakobovits, Aya. Production of fully human antibodies by transgenic mice. Cell Genesys Inc., Foster City, USA. Current Opinion in Biotechnology 1995, 6:561-566.

Kellermann & Green, Antibody discovery: the use of transgenic mice to generate human monoclonal antibodies for therapeutics. Current Opinion in Biotechnology 2002, 13:593-597.

Morrison et al. Chimeric human antibody molecules: Mouse antigenbinding domains with human constant region domains. Proc. Natl. Adad. Sci. USA. vol. 81, pp. 6851-6855, Nov. 1984.

Winter et al. Humanized antibodies. Immunology Today vol. 14 No. 6 1993. 4 pages.

U.S Appl. No. 15/026,904, filed Apr. 1, 2016. First Inventor: David Tacha.

International Application No. PCT/US14159162; filed Oct. 3, 2014. International Preliminary Report on Patentability, 6 pages. Dated Apr. 5, 2016.

European Patent App. No. 13841542.7. Extended European search report dated Apr. 28, 2016. 9 pages.

U.S. Appl. No. 15/222,690, filed Jul. 29, 2016. First Named Inventor: Weimin Qi.

U.S. Appl. No. 15/226,794, filed Aug. 2, 2016. First Named Inventor: Weimin Qi.

U.S. Appl. No. 62/306,517, filed Mar. 10, 2016. First Named Inventor: Jillian Tyrrell.

U.S. Appl. No. 15/008,069, filed Jan. 27, 2016. First Named Inventor: Weimin Qi.

U.S. Appl. No. 15/228,341, filed Aug. 4, 2016. First Named Inventor: David Tacha.

Tacha et al. "A Newly Developed Mouse Monoclonal SOX10 Antibody is a Highly Sensitive and Specifica Marker for Malignant Melanoma, Including Spindle Cell and Desmoplastic Melanomas" Archives of Pathology & Laboratory Medicine: Apr. 2015, vol. 139, No. 4, pp. 530-536; Epub Dec. 1, 2014; doi: http://dx.doi.org/10.5858/arpa.2014-0077-OA.

Harlow, E. and Lane, D., Antibodies: A Laboratory Manual (1988) Cold Spring Harbor Laboratory Press, Cold Spring Harbor, NY, pp. 23-24 and 72-76.

Van Regenmortel et al. "Molecular dissectinon of protein anitgens and the prediction of epitopes", Chaper 1 in: Laboratory Techniques in Biochemistry and molecular Biology vol. 19, 1988, pp. 1-39.

Kuby et al. Immunology, W.H. Freeman and Company (1992), p. 125.

Bost et al., "Antibodies against a peptide sequence within ght HIV envelope protein crossreacts with human interleukin-2" Immunol. Invest. 1988; 17:577-586.

Bendayan, M. "Possibilites of false immunocytochemical results generated by the use of monoclonal antibodies: the example of the anti-proinsulin" J. Histochem Ctyochem 1995; 43:881-886.

Rossi, et al., A Comparative Study between a Novel Category of Immunoreagents and the Corresponding Mouse Monoclonal Antibodies. Am. J. Clin Pathol 2005; 124, 295-302.

European Application No. 14850426.9, European Search Report dated Mar. 9, 2017. 11 pages.

U.S. Appl. No. 15/811,458, filed Nov. 13, 2017. First Named Inventor: Tacha.

Wu, et al. Uroplakin II Gene Is Expressed in Transitional Cell Carcinoma But Not in Bilharzial Bladder Squamous Cell Carcinoma: Alternative Pathways of Bladder Epithelial Differentiation and Tumor Formation. Cancer Research 28, 1291-1297, Mar. 15, 1998.

Japanese Patent Application No. 2015-534675. English Translation of the Rejection dated Aug. 2, 2017. 6 pages.

Kreitzer et al., "A robust method to derive functional neural crest cells from human pluripotent stem cells" Am J Stem Cell Jul. 15, 2013;2(2):119-131.

Kang, et al., "Diagnostic Utility of SOX10 to distinguish malignant peripheral nerve sheath tumor from synovial sarcoma, including intraneural synocial sarcoma" Modem Pathology (Jan. 1, 2014) 24, 55-61.

Santa Cruz Biotechnology, Inc. "Sox-10 (N-20): sc-17342" retrieved Feb. 20, 2017. 1 page.

Abcam "Anti-SOX10 antibody ab108408—product data sheet" Retrieved Feb. 20, 2017. 4 pages.

(56) References Cited

OTHER PUBLICATIONS

Aung, et al. "KBA62 and PNL2: Two Newer Melanoma Markers—Immunohisto-Chemical Analysis of 1563 Tumors including Metastatic, Desmoplastic, and Musocal Melanomas and their Mimics" Am J Surg Pathol Feb. 1, 2012; 36(2):265-272.
"p40 (5-17) Antibody from" © 1980-2013 Linscott's Directory. 3 pages. Date retrieved: Sep. 27, 2016.
Pelosi et al (Journal of Thoracic Oncology, 2011, 6(6)(sup 2): S335-S336) 7 pages.
Nagashio et al., Detection of tumor-specific autoantibodies in sera of patients with lung cancer (Lung Cancer, 2008, 62:364-373).
Rekhtman et al., (Modem Pathology, 2011, 24: 1348-1359).
European Patent Application No. 13841542.7, Notice of Intended Grant of Patent dated Jan. 3, 2018. 8 pages.
Kim J-K et al: Localization of the site of the murine IGG1 Molecule that is involved in binding to the murine intestinal FC Receptor European Journal of Immunology, vol. 24, No. 10, Jan. 1, 1994, pp. 2429-2434.
Ohtomo et al., SOX10 is a novel marker of acinus and intercalated duct differentiation in salivary gland tumors: a clue to this histogenesis for tumor diagnosis. Modem Pathology, 26 [Epub Apr. 2013], 1041-1050.
Tornoo Itoh, Immunohistochemistry in Diagnostic Surgical Pathology, Microscope, vol. 48, No. 1 (Apr. 2013), p. 33-38.
Multiplex IHC Antibody Cocktail, Funakoshi Co., Ltd., Aug. 30, 2012, [Retrieved on Aug. 24, 2018] web page #: 4567, Retrieved from the Internet, URL: https://www.funakoshi.co.jp/contents/4567. 5 pages.
Japanese Patent Application No. 2016-519763, English Translation of the Office Action dated Aug. 27, 2018. 10 pages.
U.S. Appl. No. 15/811,458, filed Nov. 13, 2017. Notice of Allowance dated Oct. 18, 2018. 9 pages.
European Patent Application No. 14850426.9, Office Action dated Oct. 11, 2018. 11 pages. dated Oct. 18, 2018.
Bradbury Andrew R M et al: When monoclonal antibodies are not monospecific: Hybridomas grequently express additional functional variable regions. MABS, vol. 10, No. 4, May 2018 (May 2018) pp. 539-546 ISSN:1942-0870.
Vilches-Moure, Jose et al., Comparison of Rabbit Monoclonal Antibodies in Immunohistochemistry in Canine Tissues. J Vet Diang Invest 17:346-350 (2005).
U.S. Appl. No. 14/652,407, filed Jun. 15, 2015. Office Action dated Nov. 14, 2018. 17 pages.
European Patent Application No. 14756627.7. Decision to Grant a European Patent, dated Mar. 7, 2019. 2 pages.
U.S. Appl. No. 15/811,458, filed Nov. 13, 2017. First Named Inventor: Tacha. Notice of Allowance dated Feb. 6, 2019. 5 pages.

\* cited by examiner

SYSTEMS AND METHODS FOR ANTI-UROPLAKIN III ANTIBODIES

This application is a U.S. Non-Provisional Application claiming priority to and the benefit of U.S. Provisional Application No. 61/618,279 filed Mar. 30, 2012 and U.S. Provisional Application No. 61/727,559 filed Nov. 16, 2012, each hereby incorporated by reference herein.

BACKGROUND

Microscopic examination of tissue samples, particularly those obtained by biopsy, is a common method for diagnosis of disease. In particular, immunohistochemistry (IHC), a technique in which specific antibodies are used to detect expression of specific proteins in the tissue sample, is a valuable tool for diagnosis, particularly for the detection and diagnosis of cancer.

Uroplakins (UPs) comprise a group of 4 transmembrane proteins (UPs Ia, Ib, II, and III) expressed in the luminal surface of normal urothelial superficial (umbrella) cells, which are specific differentiation products of urothelial cells. Uroplakin III (UP III) is a 47 kDa glycoprotein that may be a useful marker in cancer diagnosis. Moll et. al. reported that, when using an anti-UP III rabbit polyclonal antibody, UP III may be immunohistochemically detectable in 29 of 55 (53%) and 23 of 35 (66%) primary and metastatic urothelial carcinomas, respectively; whereas, a large number of non-urothelial carcinomas were consistently UP III-negative. (See Moll R, Wu X, Lin J, Sun T; *Am J Pathol.* 1995; 147:1383-1397, hereby incorporated by reference herein.) The authors concluded that UP III should be a valuable immunohistochemical marker, especially for the highly specific identification of urothelial carcinomas in patients with a metastatic carcinoma of unknown primary site; however, these antibodies were not readily available from commercial sources.

A mouse monoclonal antibody to Uroplakin III was developed [clone AU 1] and offered commercially by PRO-GEN, Heidelberg, Germany. In a study by Kaufmann et. al. (See Kaufmannn O, Volmerig J, Dietel M; *Am J Clin Pathol.* 2000; 113:683-687, hereby incorporated by reference herein), AU 1 was shown to be a moderately sensitive and highly specific antibody for urothelial tumors. This study demonstrated an overall sensitivity of 57% for AU 1 staining of primary and metastatic urothelial carcinomas. Importantly, this sensitivity was determined using a cut-off value of 1% of tumor cells staining positive for AU 1 as the criteria for identifying a case as positive for AU 1. Amongst practicing pathologists, such a cut-off value of 1% for determining positivity would be unusually low criteria in these types of cases. As a result, the sensitivity of AU 1 routinely observed in clinical diagnosis (where a higher cut-off, such as between about 5 and about 10% of tumor cells staining, may be the standard practice) is much lower than that reported by Kaufmann et. al. Consequently, the conclusion amongst practicing pathologists may be that AU 1 is not sufficiently sensitive to be a useful marker in the diagnosis of urothelial carcinoma and it may not be commonly used. The sensitivity reported by Kaufmann et. al. may not have been reproduced or validated in the literature in the 12 years since its publication, as may be typical for a diagnostically useful marker. It is generally known amongst pathologists that the poor sensitivity of anti-UP III (AU 1) may prevent its use as a reliable marker for TCC and a more sensitive anti-UP III antibody is desired in the field.

A clear need exists for an anti-Uroplakin III antibody with greater sensitivity than AU 1 for use in cancer diagnosis. A new anti-Uroplakin III antibody with increased staining sensitivity, while preserving equal or superior staining specificity compared to clone AU1, has been developed. Additional information may be found in patent application No. 61/706,312 filed Sep. 27, 2012 entitled "Systems and Methods for Anti-Uroplakin II Antibodies" and PCT application no. PCT/US2012/037367 filed May 10, 2012 entitled, "Systems and Methods for Anti-PAX8 Antibodies", each hereby incorporated by reference herein in their entirety.

SUMMARY OF THE INVENTION

General embodiments of the present invention may include monoclonal antibodies for recognizing UP III, methods for their preparation, use in immunohistochemistry, and the like. In embodiments, the UP III antibody clone BC17 can be obtained by immunizing Balb/C mice with a recombinant human UP III protein corresponding to amino acids 19-287, obtained by *E. coli* expression. The UP III proteins may be injected into the BALB/c mice, with an adjuvant, via subcutaneous and intraperitoneal injections alternatively, about 5 times at about three week intervals. The immune reactivity to UP III may be assessed by direct ELISA on recombinant UP III protein. Mice with the highest titer may be chosen for developing hybridomas by cell fusion. A hybridoma clone demonstrating the best reactivity to UP III on human tissues may be chosen and may be designated as BC17. The BC17 clone may be tested for isotype and may be identified as a mouse IgG2a/kappa. The BC17 antibody may be produced by large scale tissue culture of the hybridoma cells and by ascites in BALB/c mice. The supernatant and antibody ascites may be collected and the antibody may be purified by Protein A affinity column. BC17 demonstrated specific reactivity to human UP III protein by ELISA, Western blotting, and even human tissues.

This mouse monoclonal anti-UP III antibody BC17 may be useful for the detection of UP III in tissue samples, perhaps with several significant, but unexpected advantages over currently known UP III antibodies. When used in traditional immunohistochemistry procedures, the mouse UP III antibody BC17 may result in membrane or cytoplasmic staining of UP III with a specificity perhaps similar to that of known UP III antibodies. However, BC17 may exhibit increased sensitivity, perhaps as compared to past UP III antibodies, which may offer significant improvements. With BC17, analysis of the sample may be simplified and UP III expression in tumor cells may be readily identifiable, allowing diagnosis in cases that may otherwise be difficult, or not even possible, to diagnose.

DETAILED DESCRIPTION OF THE PREFERRED EMBODIMENTS

Figure 1A:
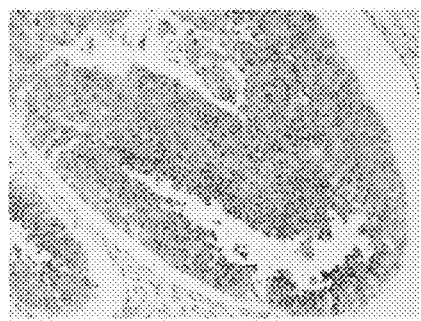
FIG. 1A shows an example of BC17 staining on bladder TCC tissue (grade 2).

As may be understood from the earlier discussion, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention may provide antibodies and methods thereof that specifically bind to UP III and may be used for the detection of UP III in the diagnosis for several types of cancers. An antibody may be an antibody fragment, a mouse monoclonal antibody, a chimeric antibody, a humanized monoclonal antibody, a human monoclonal antibody, an antibody with a label attached or even conjugated therewith or with a fragment thereof, an antibody labeled with a detectable signal or stain, an antibody labeled with a toxin, or the like. A label may include but is not limited to radioactive element, magnetic particles, radioisotope, fluorescent dye, enzyme, toxin, signal, stain, detection enzymes, horseradish peroxidase (HRP), alkaline phosphatase (AP), beta-galactosidase, chromogens, Fast Red, 3,3'-diaminobenzidine, 3-amino-9-ethylcarbazole, 5-bromo-4-chloro-3-indolyl phosphate, 3,3',5,5'-tetramethylbenzidine, 5-bromo-4-chloro-3-indolyl-β-D-glucuronide, any combination thereof, or the like. Systems and methods of the present invention may relate to the antibody or its antigen binding portion capable of binding to UP III. In other embodiments, the present invention may provide an antibody such as a monoclonal antibody or its antigen binding portion thereof capable of binding to UP III perhaps with a sensitivity greater than that of past UP III antibodies, e.g., greater than about 1%.

Mouse monoclonal antibodies may be commonly used in immunoassay methods to identify specific analytes, including as primary antibodies in immunohistochemistry procedures. Mouse monoclonal antibodies specific for the protein target of interest can be produced using generally known procedures. Generally, exposing a mouse to the antigen of interest (e.g. a peptide fragment of the desired target or the full-length protein target) may induce an immune response in which the mouse generates multiple antibodies that bind the antigen, each of which may be produced by a particular B-cell. These B-cells may be isolated from the mouse spleen and the antibodies produced may be evaluated for their suitability as primary antibodies in IHC. After selecting the optimal antibody, the associated B-cell may be fused with a tumor cell using known procedures, perhaps resulting in a hybridoma, a new cell line that can endlessly replicate and may continuously produce the desired antibody.

Monoclonal antibodies may be preferred over polyclonal antibodies for several reasons. In particular, monoclonal antibodies may be derived from a single B-cell and as such may recognize a single epitope, perhaps resulting in greater specificity. Monoclonal antibodies may also be conveniently and reproducibly generated in cell culture, perhaps resulting in a continuous supply of the desired antibody. Of course, polyclonal antibodies may be used in some embodiments.

Mouse monoclonal anti-UP III antibody BC17 may be produced using these general procedures and may be evaluated by immunohistochemistry for sensitivity and specificity on a variety of normal and neoplastic tissues, particularly in comparison to the previously known UP III antibody (AU 1).

Example of UPIII Protein Expression:

A UPIII recombinant protein may be cloned and expressed from *E. coli*. Briefly, UPIII cDNA may be cloned and purified. The UPIII cDNA may be digested by restriction enzymes and ligated into the pET30a-GST vector. BL21 cells may be transformed with the construct. The colonies expressing the correct size of recombinant protein may be selected and sequenced. A further scale up production may be performed by culturing the *E. coli* in LB media containing 0.5 mM IPTG. The final UPIII recombinant protein may be purified and analyzed by SDS-PAGE.

Example of Host Immunization:

Female BALB/c (about 6 to about 8 weeks old) mice may be immunized intraperitoneally (i.p.) with about 100 μg human UPIII protein per mouse in complete Freund's adjuvant. About three weeks later, the mice may be boosted with another 100 μg human UPIII per mouse in incomplete Freund's adjuvant about 4 more times in about 3 week intervals. Mice may be bled from the tails, and sera may be collected and stored at −20° C. for later analysis of antibody titers by enzyme-linked immunosorbant assay (ELISA).

Example of Hybridomas:

Hybridomas producing antibodies to UPIII may be generated by standard techniques from splenocytes of UPIII-immunized BALB/c mice. Briefly, splenocytes from UPIII-immunized mice may be fused to P3-X63-Ag 8.653 myeloma cells (non-secreting myeloma derived from SP2/0 Balb/c myeloma cells) by incubation with about 50% polyethylene glycol at a ratio of about 4:1. Following incubation, cells may be pelleted by centrifugation at about 3000× g for about 10 minutes, washed in about 25 ml of PBS, recentrifuged, and cell pellet may be resuspended in about 100 ml of fresh Dulbecco's Medium containing about 20% fetal bovine serum (Hyclone, Utah, Co). Aliquots of about 100 μl can be added to each well of ten 96-well microtiter plates (Corning, Lowell, Mass.). About twenty four hours later, about 100 μl DMEM culture medium supplemented with about 1M hypoxanthine (HT), about 4 mM aminopterin and about 160 mM thymidine (HAT) can be added to each microtiter well. Media may be replaced after about 4 days with complete media (perhaps containing HAT and HT). Over the following about 10 days, media may be removed and replaced with fresh media with reduced or perhaps even no HAT and HT added. Hybridoma supernatants may be screened by ELISA for antibody reactivity to UPIII, and hybridoma clones may then be selected and stabilized by cloning twice by limiting dilution.

Hybridoma cells referred to as Anti UPIII Mouse hybridoma clone BC17 Lot: 0432212 have been deposited at American Type Culture Collection (ATCC) at the address of 10801 University Boulevard, Manassas, Va., 20110-2209 USA on Mar. 23, 2012 and has received ATCC Patent Deposit Designation No. PTA-12699 as shown in the attached exhibit entitled, "Budapest Restricted Certificate of Deposit" hereby incorporated by reference herein. Embodiments of the present invention may provide an antibody or fragment thereof produced by the hybridoma deposited at the ATCC and may even include a method for producing a monoclonal antibody by culturing the hybridoma cell which produces the monoclonal antibody capable of specifically recognizing Uroplakin III and even allowing the hybridoma to produce monoclonal antibodies.

ELISA:

Host anti-sera immune responses to UPIII may be measured by ELISA. Briefly, a solution of UPIII (1 µg/ml) in phosphate-buffered saline (PBS) may be used to coat 96-well flat bottom polystyrene plates. The plates may then be blocked with about 1% bovine serum albumin (BSA)-PBS. Either diluted immune sera or hybridoma supernatants may be added and incubated at about 37° C. for about 1 hour. After washing the plates with PBS, the plates may be incubated with goat anti-mouse-HRP reagents (Jackson Labs). Incubations may be done at about 37° C. for about 30 minutes. ABTS substrate may be added to develop color and the absorbance at about 405 nm (A405) may be measured in a microtiter plate reader.

Isotype of Monoclonal Antibodies:

The BC17 monoclonal antibody may be isotyped using a mouse monoclonal antibody isotyping kit (Invitrogen, Carlsbad Calif.). Briefly, about 100 µl of supernatant from mouse monoclonal antibody [BC17] cells may be added to the plate coated goat anti mouse IgG1, IgG2A, IgG2B, IgG3, IgM, and IgA. After about 30 minutes incubation, the plate may be washed 3 times with PBS and may be incubated with goat anti mouse Ig-HRP reagent. ABTS substrate may be added to develop color and the absorbance at about 405 nm (A405) may be measured in a microtiter plate reader. The BC17 clone may be tested for isotype and may be identified as a mouse IgG2a/kappa.

Antibody Production and Purification:

The selected hybridoma cells from clone BC17 may be cultured with DMEM culture medium supplemented with about 10% FBS. The culture supernatants may be further purified by protein A affinity column. The hybridoma cells may also be injected into pristane-primed BALB/c mice to produce antibody ascites. The antibody ascites may be further purified by protein A affinity column. IgG concentration may be measured spectrophotometrically using the extinction coefficient for human IgG of about 1.4 (about 0.1% at about 280 nm). The purity of IgG may be determined by SDS-PAGE.

Western Blotting:

The purified monoclonal antibody [BC17] may be characterized by Western Blotting. Whole-cell lysates may be generated from RT4 cells with lysis buffer (about 1% NP40, about 0.5% sodium deoxycholate, and about 0.1% SDS in PBS) in the presence of protease inhibitors. Lysate (between about 20 and about 30 µg/lane) may be subjected to protein gel electrophoresis using about 4 to about 12% SDS-PAGE with Tris-glycine buffer and may be transferred onto nitrocellulose filters in Tris-glycine buffer. Proteins on the blots may be visualized by incubating BC17 antibody for about 60 minutes in room temperature after blocking with blocking buffer, followed by incubating with peroxidase-conjugated goat anti-mouse immnoglobulins.

Determination of VH and VL Sequences:

Total RNA may be extracted from hybridomas using Qiagen kit (USA, Gaithersburg, Md.) as per the manufacturer's instructions. First-round RT-PCR may be carried out with QIAGEN® OneStep RT-PCR Kit. RT-PCR may be performed with primer sets specific for the heavy and light chains. For each RNA sample, about 12 individual heavy chain and about 11 light chain RT-PCR reactions can be set up using degenerate forward primer mixtures covering the leader sequences of variable regions. Reverse primers may be located in the constant regions of heavy and light chains. No restriction sites may be engineered into the primers. The RT-PCR products from the first-round reactions may be amplified in the second-round PCR. About 12 individual heavy chain and about 11 light chain RT-PCR reactions can be set up using semi-nested primer sets specific for antibody variable regions. The amplified cDNAs can be gel purified and may then be sequenced.

BC17 variable domains were sequenced to provide isolated polynucleotides that comprise nucleic acid sequences encoding the amino acid sequences of one or more of the CDRs of the light and/or heavy chain variable regions of a monoclonal antibody described herein that binds to the UP III epitope SLPFFLLVG identified as SEQ ID NO: 3. The sequence of the variable region of the heavy chain is identified as SEQ ID NO: 1 and the sequence of the variable region of the light chain is identified as SEQ ID NO: 2. An antibody or fragment thereof may include a polypeptide of the amino acid sequence encoded by the nucleic acid sequence of SEQ ID NO: 1 and/or SEQ ID NO: 2. An antibody or fragment thereof may include a light chain variable region having an amino acid sequence encoded by the nucleic acid sequence of SEQ ID NO: 2 and may even include a heavy chain variable region having an amino acid sequence encoded by a nucleic acid sequence of SEQ ID NO: 1. An antibody or fragment thereof may specifically bind to at least one polypeptide of an amino acid sequence of SEQ ID NO: 3. As mentioned herein, a fragment thereof may include an antigen binding fragment thereof.

In embodiments, an antibody or fragment thereof, or even an isolated and purified nucleic acid sequence may have an amino acid sequence of at least about 70% identical to an amino acid sequence encoded by a nucleic acid sequence of SEQ ID NO: 1 and/or SEQ ID NO: 2. An antibody or fragment thereof may specifically binds to at least one polypeptide with an amino acid sequence that is at least about 70% identical to residues of SEQ ID NO: 3. Other percentages may include, but are not limited to, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, and perhaps even at least about 99%, or the like.

Epitope Mapping of the Mouse Anti-UPIII [BC17] Binding Sequence:

In order to determine the peptide sequence of UP III that is recognized by BC17, epitope mapping may be conducted using two assays: direct ELISA and dot blot. In an ELISA assay, the sensitivity and specificity of the anti-UP III [BC17] antibody may be determined by measuring the antibody titer at about 1:500 and about 1:1000. Overlapping peptides at a length of about 15 amino acids each, covering the full length of the human UP III protein, may be used to determine the preferred sequence of BC17 binding.

The epitope for BC17 was shown to be included in the residues 217-225 amino acid of UPIII, which is SLPFFLLVG identified as SEQ ID NO: 3. The epitope of the mouse monoclonal UPIII antibody, or a portion thereof, may be a useful antigen for the production of new monoclonal antibodies, including production in species other than mouse (e.g. rabbit, goat, horse, chicken, etc.). Of course, a polyclonal antibody may be provided with this epitope in other embodiments. An isolated preparation of antibodies may specifically bind to an epitope in SEQ NO: 3 which relates to residues 217-225 of the Uroplakin III protein.

For direct ELISA protocol, the plates may be first coated with 100 µl of UP III peptides at about 5 µg/mL in coating buffer (pH about 9.5) overnight at 4° C., followed by blocking (about 3% BSA) at about 200 µl/well for 1 hour at room temperature. The plates may be incubated with purified UP III antibody at about 100 ng/mL and about 200 ng/mL separately for about 1 hour at room temperature on an ELISA-plate shaker. Then the plates may be washed five times with PBST (about 300 µl/well) followed by the addition of goat anti-mouse IgG-HRP to the plates and incubation for 1 hour on a plate-shaker. The plates may then be washed with PBST (about 300 µl/well) and blotted to dry, and TMB may be added at about 100 µl/well, developed for about 5 min on a shaker, followed by a stop solution (about 50 µl/well). Absorbance may be measured at about 450 nm on an ELISA plate reader according to the manufacturer's recommendation.

For the dot blot assay, a nitrocellulose membrane may be blotted with about 1 µl at a concentration of about 1 mg/ml the peptide, quadruplicates per peptide. This membrane may be incubated for about 1 hour at room temperature until it is completely dry. The membrane may be blocked with about 3% BSA in TBST (about 50 mM Tris, about 0.5 M NaCl, about 0.05% TWEEN® 20, aka polysorbate 20, a polysorbate surfactant, pH about 7.4) for about 1 hour at room temperature, then mouse anti UP III antibody [BC17] may be added at about 200 ng/ml for about 1 hr at RT in TBST. Then the membrane may be washed for about 3 times (about 10 minutes each) in TBST on an orbital shaker, followed by incubating with secondary antibody goat anti mouse IgG1-AP for about 1 hour at room temperature in TBST. The membrane may be washed about 3 times (about 10 minutes each) in TBST on a rocker. The binding may be detected by adding Western Glo Chemiluminescent detection reagents and exposing to film.

IHC Method with Anti-UP III BC17:

Immunohistochemistry using the mouse monoclonal UP III antibody BC17 may be performed on formalin-fixed paraffin embedded (FFPE) tissue samples using procedures generally known to those in the art, as generally exemplified by the following non-limiting examples (washes with Tris-buffered saline, pH about 7.6, between steps):

1) Sections (~5 µm) of formalin fixed paraffin-embedded tissues may be mounted on commercially available microscope slides coated with polylysine.
2) Sections may be deparaffinized (using xylenes or a xylene-substitute) and may be rehydrated through a series of alcohol/water solutions, followed by blocking of endogenous peroxidases with about 3% hydrogen peroxide solution.
3) Samples may be subjected to heat-induced antigen retrieval using a citrate buffer in a pressure cooker (Reveal, Decloaking Chamber; Biocare Medical) and may be heated to about 125° C. for about 30 seconds. [Other antigen retrieval methods known to those skilled in the art (e.g., steamer, microwave oven, and enzyme) may also be acceptable.] Tissues may be allowed to cool for about 10 minutes and then may be rinsed with deionized water.
4) The UP III antibody BC17 may be applied in a phosphate-buffered solution (pH about 6.0) with bovine serum albumin as carrier protein for about 30 minutes.
5) Detection of the UP III antibody with a horseradish peroxidase (HRP) conjugated secondary antibody (MACH 4 Universal HRP-Polymer Detection, Biocare Medical) may be accomplished in two steps. An initial application of a rabbit anti-mouse IGg antibody for about 10 minutes may be followed by incubation with a goat anti-rabbit-HRP conjugate for about 10 minutes.
6) In a final detection step, 3,3'-diaminobenzidine (DAB) in buffer containing about 0.02% hydrogen peroxide (Betazoid DAB, Biocare Medical) may be applied. The oxidation of DAB through an HRP-mediated mechanism may result in precipitation of a brown, chromogenic product, perhaps allowing identification of sites of UP III expression.
7) Slides may be briefly counterstained in a modified Mayer's hematoxylin.

Results of IHC Staining with Mouse Monoclonal Anti-UP III Antibody BC17:

Using the above protocol, a variety of normal and neoplastic tissues were evaluated for UP III expression using BC17 and compared to staining patterns using a mouse monoclonal anti-UP III antibody (AU 1, PROGEN). Both antibodies were optimized for titer (e.g., concentration) using methods well known to those in the art. Briefly, various antibody titers were evaluated to maximize staining intensity, while minimizing or eliminating background staining. For each antibody, the titer that provided the maximum staining intensity, with the minimal background staining, was used.

FIGS. 1-4 shows several examples of staining of bladder transitional cell carcinoma by BC17, in comparison to staining with AU 1, on a serial section of the same specimen.

Table 1 shows the sensitivity of BC17 staining 178 specimens of bladder cancer (e.g., transitional cell carcinoma (TCC), or urothelial carcinoma), using a tissue microarray (TMA). Employing a cut-off of ≥ about 5% of tumor cells staining as the criteria to determine a case as "positive" for UP III, and conversely <about 5% of tumor cells staining as the criteria to determine a case "negative," 97 of 178 (54%) were found to be positive for UP III with BC17. Diagnosis of tumors of higher grade can sometimes be a challenge. In these specimens, BC17 identified 46 of 78 (59%) of Grade II tumors, and 18 of 41 (42%) of Grade III tumors.

TABLE 1

UP III (BC17) on Bladder cancer (TCC) TMA

| Grade | Number of Specimens | Number of Positive Specimens | % Positive | Number of Negative Specimens | % Negative |
|---|---|---|---|---|---|
| Grades I, II & III | 178 | 97 | 54% | 81 | 46% |
| Grade II | 78 | 46 | 59% | 32 | 41% |
| Grade III | 43 | 18 | 42% | 25 | 58% |

The greater sensitivity of BC17, compared to AU 1, was demonstrated by staining the same 59 specimens of TCC of Grades I, II and III with each antibody (Table 2). Using the same criteria, BC17 identified 33 specimens as positive (56%), compared to 18 specimens (31%) determined to be positive with AU 1. In Grade II specimens, BC17 and AU 1 demonstrated sensitivities of 53% (19 of 36) and 23% (9 of 36), respectively. In Grade III specimens, BC17 and AU 1 demonstrated sensitivities of 64% (7 of 11) and 36% (4 of 11), respectively. In each comparison, BC17 was more sensitive than AU 1. Importantly, every specimen that was positive with AU 1 was also positive with BC17.

TABLE 2

Comparison of UP III antibodies BC17 and AU 1 on Bladder cancer (TCC) TMA

| Antibody | Grade | Number of Specimens | Number of Positive Specimens | % Positive | Number of Negative Specimens | % Negative |
|---|---|---|---|---|---|---|
| BC17 | Grades I, II & III | 59 | 33 | 56% | 26 | 44% |
| AU 1 | Grades I, II & III | 59 | 18 | 31% | 41 | 69% |
| BC17 | Grade II | 36 | 19 | 53% | 17 | 47% |
| AU 1 | Grade II | 36 | 9 | 25% | 27 | 75% |
| BC17 | Grade III | 11 | 7 | 64% | 4 | 36% |
| AU 1 | Grade III | 11 | 4 | 36% | 7 | 64% |

BC17 was found to be highly specific when evaluated on a variety of normal (Table 3) and neoplastic (Table 4) tissues. Bladder was the only normal tissue to stain positive with BC17. Such staining is expected, considering the known expression of UP III in normal urothelium. BC17 did not stain any other normal or neoplastic tissues, perhaps demonstrating its high specificity.

TABLE 3

BC17 staining of normal tissues

| Tissue | # cases | Number of positive cases |
|---|---|---|
| Bladder | 6 | 6 |
| Brain | 6 | 0 |
| Adrenal gland | 3 | 0 |
| Ovary | 3 | 0 |
| Pancreas | 3 | 0 |
| Parathyroid gland | 3 | 0 |
| Hypophysis | 3 | 0 |
| Testis | 3 | 0 |
| Thyroid | 3 | 0 |
| Breast | 3 | 0 |
| Spleen | 3 | 0 |
| Tonsil | 3 | 0 |
| Thymus gland | 3 | 0 |
| Bone marrow | 3 | 0 |
| Lung | 6 | 0 |
| Heart | 3 | 0 |
| Esophagus | 3 | 0 |
| Stomach | 3 | 0 |
| Small intestine | 3 | 0 |
| Colon | 3 | 0 |
| Liver | 3 | 0 |
| Salivary gland | 3 | 0 |
| Kidney | 3 | 0 |
| Prostate | 3 | 0 |
| Uterus | 6 | 0 |
| Cervix | 3 | 0 |
| Endometrium | 3 | 0 |
| Skin | 6 | 0 |
| Skeletal muscle | 6 | 0 |
| Nerve | 6 | 0 |
| Mesothelium | 3 | 0 |
| Retina | 3 | 0 |
| Larynx | 3 | 0 |

TABLE 4

BC17 staining of various tumor tissues

| Tumor Type | Number of cases | Number of Positive Cases |
|---|---|---|
| Glioblastoma | 1 | 0 |
| Meningioma | 1 | 0 |
| Epindymoma | 1 | 0 |
| Oligodendroglioma | 1 | 0 |
| Ovarial serous adenocarcinoma | 1 | 0 |
| Ovarial Mucinous adenocarcinoma | 1 | 0 |
| Pancreatic Islet cell carcinoma | 1 | 0 |
| Pancreatic adenocarcinoma | 1 | 0 |
| Seminoma | 1 | 0 |
| Embryonal carcinoma | 1 | 0 |
| Medullary carcinoma | 1 | 0 |
| Thyroid carcinoma | 1 | 0 |
| Breast intraductal carcinoma | 3 | 0 |
| Diffuse large B-cell lymphoma | 3 | 0 |
| Lung small cell carcinoma | 1 | 0 |
| Lung squamous cell carcinoma | 1 | 0 |
| Lung adenocarcinoma | 1 | 0 |
| Esophahus squamous cell carcinoma | 1 | 0 |
| Esophagus adenocarcinoma | 1 | 0 |
| Stomach mucinous adenocarcinoma | 1 | 0 |
| Colon adenocarcinoma | 2 | 0 |
| Malignant interstitialoma | 3 | 0 |
| Rectum adenocarcinoma | 1 | 0 |
| Hepatocellular carcinoma | 1 | 0 |
| Hepatoblastoma | 1 | 0 |
| Kidney clear cell carcinoma | 1 | 0 |
| Prostate adenocarcinoma | 2 | 0 |
| Leiomyoma | 1 | 0 |
| Leiomyosarcoma | 2 | 0 |
| Endometrial adenocarcinoma | 1 | 0 |
| Uterus clear cell carcinoma | 1 | 0 |
| Cervical squamous cell carcinoma | 2 | 0 |
| Rhabdomyosarcoma | 2 | 0 |
| Melanoma | 2 | 0 |
| Basal cell carcinoma | 1 | 0 |
| Skin squamous cell carcinoma | 1 | 0 |
| Neurofibroma | 1 | 0 |
| Ganglioneuroblastoma | 1 | 0 |
| Mesothelioma | 1 | 0 |
| Hodgkin's lymphoma | 1 | 0 |
| Osteosarcoma | 1 | 0 |

BC17 was further evaluated in numerous specimens of various normal and neoplastic tissues (Table 5).

TABLE 5

BC17 staining of various normal and neoplastic tissues

| Type of Tissue | Number of cases | Number of positive cases |
|---|---|---|
| Kidney clear cell carcinoma | 48 | 0 |
| Kidney granular cell carcinoma | 13 | 0 |
| Normal Kidney | 3 | 0 |
| Breast Ductal Carcinoma | 144 | 0 |
| Breast Lobular Carcinoma | 24 | 0 |
| Normal Breast | 40 | 0 |

TABLE 5-continued

BC17 staining of various normal and neoplastic tissues

| Type of Tissue | Number of cases | Number of positive cases |
| --- | --- | --- |
| Pancreatic adenocarcinoma | 59 | 0 |
| Pancreatic squamous cell carcinoma | 1 | 0 |
| Normal pancreas | 20 | 0 |
| Seminoma | 71 | 0 |
| B-cell lymphoma | 8 | 0 |
| T-cell lymphoma | 1 | 0 |
| Lung adenocarcinoma | 24 | 0 |
| Lung squamous cell carcinoma | 25 | 0 |
| Lung adenosquamous cell carcinoma | 4 | 0 |
| Small cell lung cancer | 10 | 0 |
| Large cell lung cancer | 2 | 0 |
| Alveolar cell lung cancer | 3 | 0 |
| Lung carcinoid | 2 | 0 |
| Normal lung | 3 | 0 |
| Colon adenocarcinoma | 57 | 0 |
| Colon squamous cell carcinoma | 1 | 0 |
| Normal colon | 3 | 0 |
| Prostate adenocarcinoma | 40 | 0 |
| Normal prostate | 8 | 0 |
| Ovarian serous papillary carcinoma | 40 | 0 |
| Ovarian mucinous papillary carcinoma | 1 | 0 |
| Ovarian clear cell carcinoma | 6 | 0 |
| Ovarian granular cell carcinoma | 2 | 0 |
| Ovarian metastatic adenocarcinoma | 6 | 0 |
| Ovarian metastatic signet-ring cell carcinoma | 3 | 0 |
| Ovarian endodermal sinus carcinoma | 2 | 0 |
| Ovarian dysgerminoma | 3 | 0 |
| Ovarian mixed germ cell tumor | 1 | 0 |
| Normal ovary | 10 | 0 |

Figure 1B:
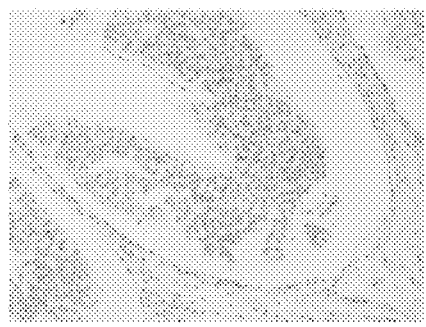
FIG. 1B shows an example of AU 1 staining on a serial section of the same bladder TCC tissue of FIG. 1A.
Figure 2A:
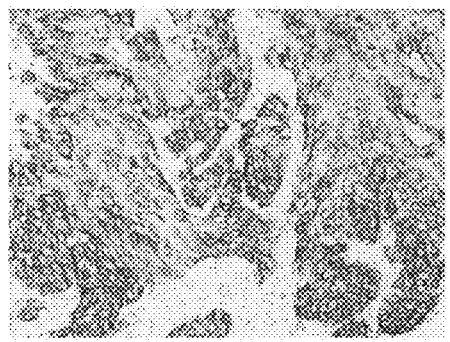
FIG. 2A shows an example of BC17 staining on bladder TCC tissue (grade 2).
Figure 2B:
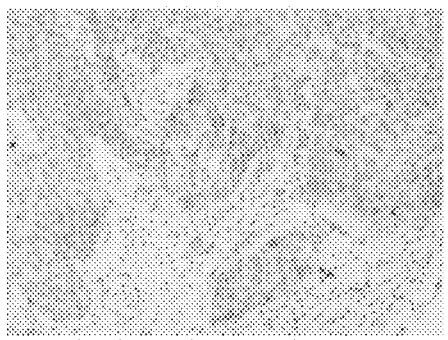
FIG. 2B shows an example of AU 1 staining on a serial section of the same bladder TCC tissue of FIG. 2A.
Figure 3A:
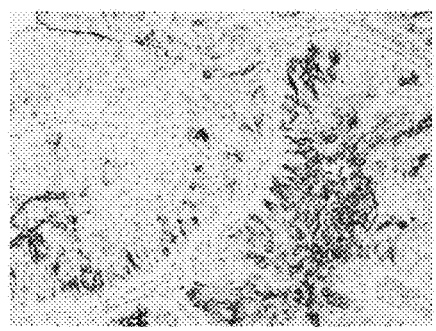
FIG. 3A shows an example of BC17 staining on bladder TCC tissue (grade 2).
Figure 3B:
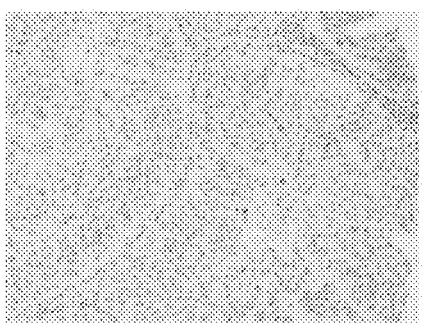
FIG. 3B shows an example of AU 1 staining on a serial section of the same bladder TCC tissue of FIG. 3A.
Figure 4A:
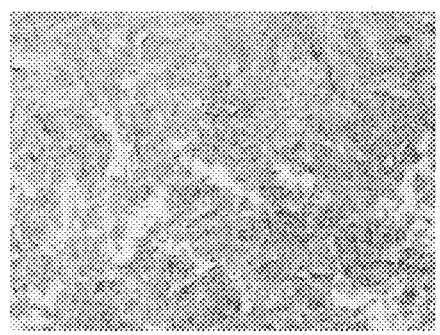
FIG. 4A shows an example of BC17 staining on bladder TCC tissue (grade 3).
Figure 4B:
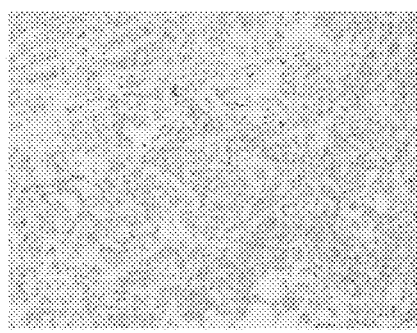
FIG. 4B shows an example of AU 1 staining on a serial section of the same bladder TCC tissue of FIG. 4A.
Figure 5:
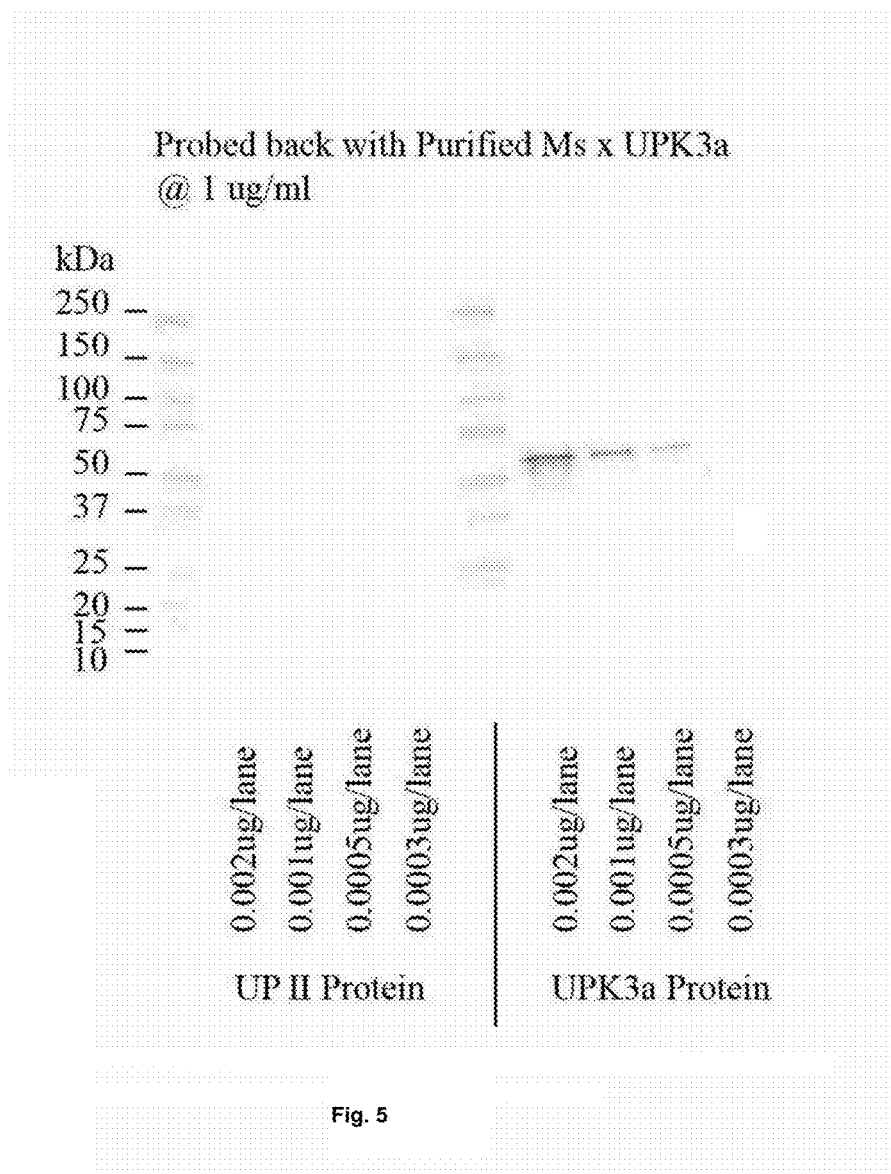
FIG. 5 shows a Western Blot of anti-UPIII antibody BC17 with Uroplakin II protein (left lanes) and Uroplakin III protein (right lanes).

The monoclonal mouse UP III antibody BC17 may offer distinct advantages with its improved sensitivity, compared to AU 1. FIGS. 1-4 show comparisons of BC17 with AU 1 staining serial sections of the same specimen of bladder TCC, demonstrating the greater sensitivity of BC17. For example, the specimen of FIG. 1 exhibited strong membrane staining with BC17 (FIG. 1A), while AU 1 was completely negative in this case (FIG. 1B). In FIG. 2, strong, widespread staining of BC17 was observed (FIG. 2A); whereas only sparse, focal staining was observed on the same specimen with AU 1 (FIG. 2B). Similarly, the specimen of FIG. 3 displayed strong staining with BC17 (FIG. 3A), but only limited focal staining with AU 1 (FIG. 3B). Finally, FIG. 4 shows a specimen that also exhibited strong staining with BC17 (FIG. 4A); in contrast, AU 1 was negative on this same specimen (FIG. 4B).

These examples demonstrate cases where a pathologist may have been able to definitively identify the presence of urothelial carcinoma with BC17, which would not have been possible with a less sensitive antibody, such as AU 1 (FIGS. 1 and 4). Or, the ambiguous results with AU 1 may have led to an equivocal diagnosis that lacks confidence, whereas BC17 offered a clear, unambiguous result (FIGS. 2 and 3).

The focal staining observed with AU 1 in FIGS. 2 and 3 are excellent examples of the challenge that may be faced by pathologists when using a less sensitive antibody; specifically, when the staining observed is sparse and light, it may be difficult to determine with confidence if this is true positive staining, signaling the presence of UP III and indicative of urothelial carcinoma, or if it is a misleading staining artifact and should be dismissed. The ambiguity associated with a less sensitive antibody may lead to equivocal, or incorrect diagnoses and patients with urothelial carcinoma may not receive appropriate treatment in a timely fashion. In contrast, BC17 may offer a significant advantage for diagnosis with its increased sensitivity. BC 17 may result in strong, clear staining of urothelial carcinoma that may allow a pathologist to definitively return a diagnosis of urothelial carcinoma, allowing a patient to expeditiously receive the most appropriate treatment.

In some embodiments of the present invention, the mouse monoclonal UP III antibody BC17 may be suitable for use in many variations of the above protocols and other methods known to those in the art. Specimens stained with BC17 may be archived using a permanent mounting media and a coverslip. The antibody BC17 may also be used in an automated staining instrument, using standard protocols. One can also envision the use of many alternative detection methods (e.g., fluorescence), detection enzymes (e.g., alkaline phosphatase (AP), beta-galactosidase), and perhaps even chromogens (e.g., 3-amino-9-ethylcarbazole, 5-bromo-4-chloro-3-indolyl phosphate, 3,3',5,5'-tetramethylbenzidine, 5-bromo-4-chloro-3-indolyl-β-D-glucuronide), generally known to those in the art.

The epitope of the mouse monoclonal UP III antibody, or a portion thereof, may be a useful antigen for the production of new monoclonal antibodies, including production in species other than mouse (e.g. rabbit, goat, horse, chicken, etc.). A monoclonal antibody for Uroplakin III may include but is not limited to a mouse monoclonal antibody, a rabbit monoclonal antibody, a goat monoclonal antibody, a horse monoclonal antibody, a chicken monoclonal antibody, a humanized monoclonal antibody, a chimeric antibody, any combination thereof, or the like. In other embodiments, a polyclonal antibody for Uroplakin III may include but is not limited to rabbit polyclonal antibody, mouse polyclonal antibody, a goat polyclonal antibody, a horse polyclonal antibody, a chicken polyclonal antibody, a humanized polyclonal antibody, any combination thereof, or the like. In yet other embodiments, an antibody may be an isolated antibody.

While the use of BC17 in immunohistochemistry of formalin-fixed paraffin embedded tissues is described here, its utility in other immunoassays may be readily envisioned and are meant to be included in this application. In particular, it may be well known that many of the same reagents used in IHC of FFPE may also be used in IHC of frozen-tissue sections. BC17 may also be useful in other immunoassays, including ELISA, perhaps using generally known methods.

In another aspect of the invention, perhaps related to IHC, a UPIII antibody may be used in conjunction with one or more additional primary antibodies as part of a cocktail, to perform a "double-stain" procedure (also described as multi-stain or even multiplex). Such "double-stain" procedures may be generally well known in the art; however, the best combinations of primary antibodies for a particular diagnostic application may not be known.

In this method, UPIII antibodies such as a mouse monoclonal UPIII antibody BC17 could be combined with one or more antibodies in a primary antibody cocktail, perhaps suitable for simultaneous application to a specimen. The antibodies may be derived from a at least two different species such as but not limited to a mouse host or a rabbit host or the like. Species may include but is not limited to mouse, rabbit, goat, horse, chicken, human, any combination thereof, or the like. The antibodies may be monoclonal or polyclonal. In embodiments, an antibody cocktail may be used in a double-stain IHC procedure to perhaps produce two or more colored stains that may identify the presence or absence of target protein antigens in the tissue specimen. For example, in embodiments where an antibody cocktail may be comprised of mouse and rabbit antibodies, a detection system may include an anti-mouse antibody conjugated to horseradish peroxidase (HRP) and perhaps even an anti-rabbit antibody conjugated to alkaline phosphatase (AP) may be used to produce the two-color stain. 3,3'-diaminobenzidine (DAB) may be used to produce a brown stain, perhaps facilitated by HRP, and it may identify the presence or absence, and/or location, of mouse antibodies bound in the specimen; Fast Red may be used to produce a fuchsia/red stain, perhaps facilitated by AP, and it may identify the presence or absence, and/or location, of rabbit antibodies in the specimen. In other embodiments, a detection system may include an anti-mouse antibody conjugated to AP and an anti-rabbit antibody conjugated to HRP which may be used to produce a two-color stain that may identify the presence or absence, and/or location of the mouse antibodies with a red stain and the rabbit antibodies with a brown stain, perhaps when Fast Red and DAB may be used as chromogens. In some embodiments, a first antibody conjugated to HRP and perhaps a second antibody conjugated to AP may be applied to the specimen as a cocktail, in a single solution, or they may be applied in separate, sequential steps.

The anti-mouse or anti rabbit antibodies comprising the antibody-enzyme conjugates may be derived from a different host species, including, but not limited to mouse, rabbit, chicken, horse, rat, goat, sheep, or the like. A primary antibody may be from a variety of host species, including, but not limited to mouse, rabbit, chicken, horse, rat, goat, sheep, or the like. In embodiments, an antibody may include an antibody-enzyme conjugate and a primary antibody could be obtained from two different host species. Chromogens other than DAB and/or Fast Red may be used as well.

Multiple alternatives to a double-staining method are possible, including but not limited to the use of more than two antibodies, the use of species other than mouse and rabbit, other chromogens and detection systems, a different order of detection steps, and perhaps even modifications resulting in three or more colors (which may require a denaturing step).

Embodiments of the present invention may provide a composition having at least two antibodies or fragments thereof, perhaps as a cocktail, where at least one of the two antibodies or fragments thereof specifically binds to at least Uroplakin III. This may provide a method for detecting at least two different proteins in a biological sample perhaps by contacting a biological sample with a composition comprising at least two antibodies or fragments thereof, where at least one of the at least two antibodies or fragments thereof may bind specifically to at least Uroplakin III, to form an antigen-antibody complex and an antigen-antibody complex may be detected. A composition may have at least one first primary antibody and at least one second primary antibody.

At least one of the antibodies or fragments thereof may specifically bind to at least Uroplakin III and may even have a positive indication cut-off value of greater than 1% of stained cells. As mentioned herein, a positive indication cut-off value may provide a percentage of stained cells needed to indicate a positive staining result. Other cut-off value may include but are not limited to greater than about 1% of stained cells, greater than about 2% of stained cells, greater than about 3% of stained cells, greater than about 4% of stained cells, greater than about 5% of stained cells, greater than about 6% of stained cells, greater than about 7% of stained cells, greater than about 8% of stained cells, greater than about 9% of stained cells, and perhaps even greater than about 10% of stained cells, or more, or the like.

In embodiments, the present invention may provide a composition with at least two antibodies or fragments thereof which may be capable of providing different visualization results such as different color results. As discussed in other embodiments, below, a composition may provide that at least one other of an at least two antibodies or fragments thereof may bind specifically to GATA-3, p63, Uroplakin II, PAX8, NKX3.1, ERG, PSA, any combination thereof, or the like. Antibodies, compositions thereof, perhaps with anti-Uroplakin III antibodies may provide a detection system including but not limited to urothelial carcinoma detection composition, basal cells in prostate gland detection composition, renal cell carcinoma detection composition, prostate carcinoma detection composition, ovarian cancer detection, any combination thereof, or the like.

In some embodiments, a single color stain may be used for a primary antibody cocktail. In one example, if the primary antibody cocktail is comprised of antibodies all derived from the same host species, then a single antibody enzyme conjugate may be used to stain for the presence of all of the antibodies with a single color. The presence or absence of each antibody may be determined based on cellular localization, or perhaps such determination is not necessary and the staining may be interpreted effectively without identifying the presence or absence of each individual antibody.

Certain steps of an IHC procedure may be performed sequentially or simultaneously, perhaps by using a cocktail of reagents, as known to those skilled in the art. For example, antibodies described in a primary antibody cocktail may alternatively be applied in sequential steps of one or more antibodies. Similarly, detection reagents may be applied simultaneously in reagent cocktail or separate reagents in sequential steps.

In some embodiments, a first primary antibody may be applied, followed by a first antibody-enzyme conjugate and first chromogen, and then a denaturing step, before proceeding to application of a second primary antibody, followed by a second antibody-enzyme conjugate and a second chromogen. In this manner, a double-stain of two different colors may be achieved using primary antibodies derived from the same species.

Antibodies that may be useful for diagnosis when combined with an UPIII antibody such as a mouse monoclonal UPIII antibody BC17 in a primary antibody cocktail for use in multi-stain procedures can include:

TABLE 6

| Antibody Cocktail | Utility |
| --- | --- |
| UP III + GATA-3 | Urothelial marker of enhanced sensitivity |
| UP III + p63 | Urothelial marker of enhanced sensitivity |
| UP III + UP II | Urothelial marker of enhanced sensitivity |
| UPIII + PAX8 | Differential marker of bladder and kidney |
| UPIII + NKX3.1 | Differential marker of bladder and prostate |
| UPIII + ERG | Differential marker of bladder and prostate |
| UPIII + GATA-3 and/or p63 + PAX8 + PSA and/or NKX3.1 | Differential marker of bladder, kidney, and prostate cancer |

Alternative embodiments of antibodies that may be useful for diagnosis when combined with an UPIII antibody such as a mouse monoclonal UPIII antibody BC17 in a primary antibody cocktail for use in multi-stain procedures can include:

TABLE 7

Figure 9A:
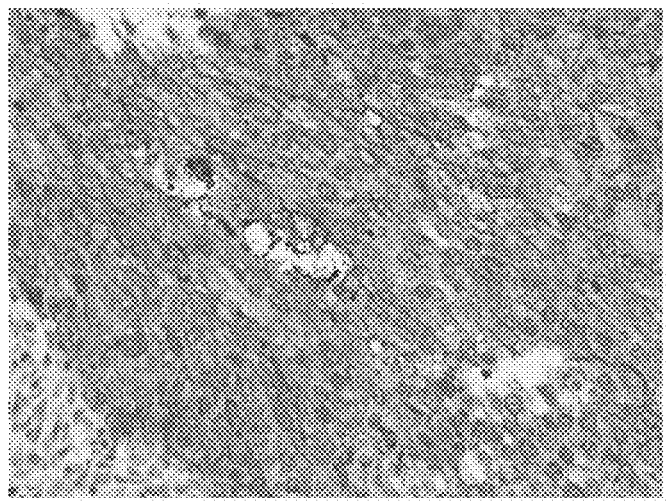
FIG. 9A shows an example of a cocktail of UPIII+ GATA3+PAX8 staining urothelial carcinoma. In this example, staining of both UPIII (brown, membranous & cytoplasmic) and GATA3 (brown, nuclear) is observed. No staining of PAX8 (red) is observed.
Figure 9B:
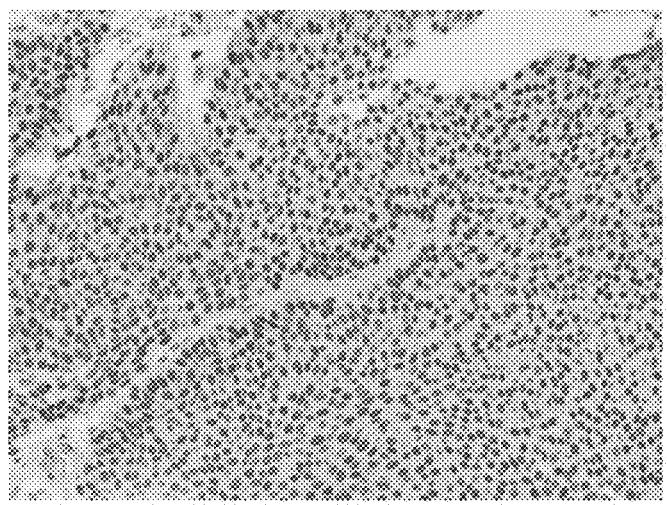
FIG. 9B shows an example of a cocktail of UPIII+ GATA3+PAX8 staining urothelial carcinoma. In this example, staining of GATA3 (brown, nuclear) observed. No staining of PAX8 (red) is observed.
Figure 10A:
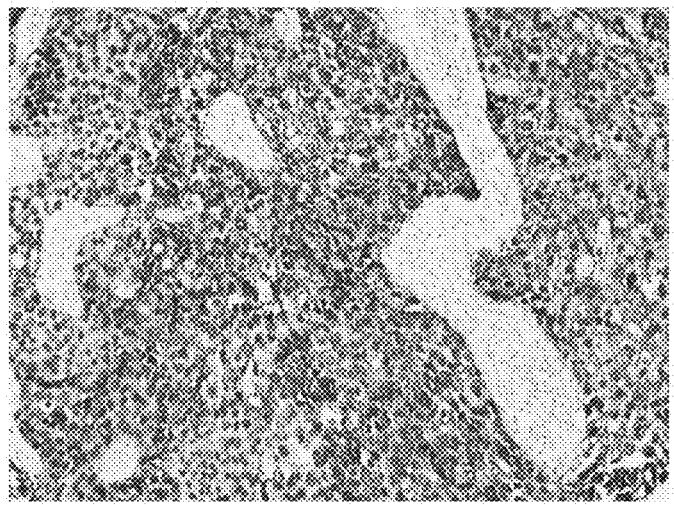
FIG. 10A shows an example of a cocktail of UPIII+ GATA3+PSA staining urothelial carcinoma. Staining of UPIII (brown) is membranous and cytoplasmic and staining of GATA3 is nuclear (brown). No other cytoplasmic staining of PSA (red) is observed.
Figure 10B:
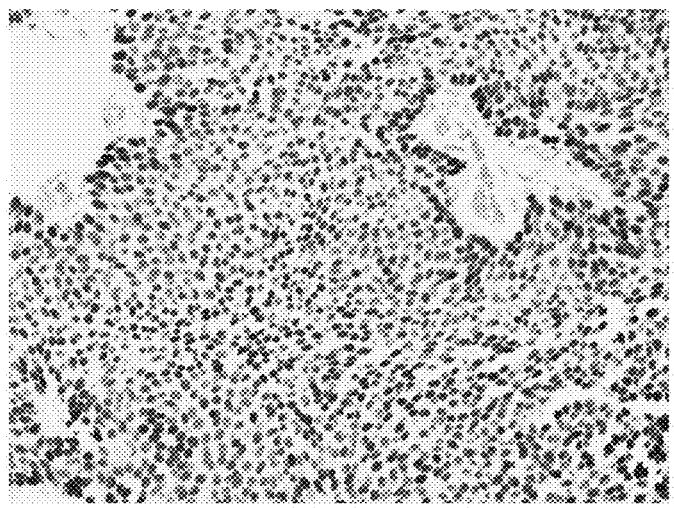
FIG. 10B shows an example of a cocktail of UPIII+ GATA3+PSA staining urothelial carcinoma. Staining GATA3 is nuclear (brown). No other nuclear staining of UPIII (brown) or cytoplasmic staining of PSA (red) is observed.

| Antibody Combination (Host Species, cellular localization, stain color*) | Possible Diagnostic Utility | Detection System used in example and FIG. No. |
|---|---|---|
| UPIII (Mouse, Membrane & cytoplasmic, brown) UPII (Mouse, Membrane & cytoplasmic, brown) | UPII and/or UPIII staining may be observed in urothelial carcinoma | DS #2 FIG. 6 |
| UPIII (Mouse, Membrane & cytoplasmic, brown) p63 (Mouse, Nuclear, brown) | UPIII staining may be observed in urothelial carcinoma; p63 staining may be observed in urothelial carcinoma | DS #2 FIG. 7 |
| UPIII (Mouse, Membrane & cytoplasmic, brown) PAX8 (Mouse, Nuclear, brown) | UPIII staining may be observed in urothelial carcinoma; PAX8 staining may be observed in renal cell carcinoma or ovarian carcinoma | DS #2 FIG. 8 |
| UPIII (Mouse, Membrane & cytoplasmic, brown) GATA3 (Mouse, Nuclear, brown) PAX8 (Rabbit, Nuclear, red) | UPIII staining may be observed in urothelial carcinoma; GATA3 staining may be observed in urothelial carcinoma; PAX8 staining may be observed in renal cell carcinoma or ovarian carcinoma | DS #2 FIG. 9 |
| UPIII (Mouse, Membrane & cytoplasmic, brown) GATA3 (Mouse, Nuclear, brown) PSA (Rabbit, Cytoplasmic, red) | UPIII staining may be observed in urothelial carcinoma; GATA3 staining may be observed in urothelial carcinoma; PSA staining may be observed in prostate cancer or normal prostate | DS #2 FIG. 10 |
| UPIII (Mouse, Membrane & cytoplasmic, brown) ERG (Mouse, Nuclear, brown) | UPIII staining may be observed in urothelial carcinoma; ERG staining may be observed in prostate cancer (as well as in normal endothelial cells) | DS #2 FIG. 11 |
| UPIII (Mouse, Membrane & cytoplasmic, brown) NKX3.1 (Rabbit, Nuclear, red) | UPIII staining may be observed in urothelial carcinoma; NKX3.1 staining may be observed in prostate cancer or normal prostate | DS #2 FIG. 12 |
| UPIII (Mouse, Membrane & cytoplasmic, red) ERG (Mouse, Nuclear, red) NKX3.1 (Rabbit, Nuclear, brown) | UPIII staining may be observed in urothelial carcinoma; ERG staining may be observed in prostate cancer (as well as in normal endothelial cells); NKX3.1 staining may be observed in prostate cancer or normal prostate | DS #1 FIG. 13 |
| UPIII (Mouse, Membrane & cytoplasmic, red) ERG (Mouse, Nuclear, red) PSA (Rabbit, Cytoplasmic, brown) | UPIII staining may be observed in urothelial carcinoma; ERG staining may be observed in prostate cancer (as well as in normal endothelial cells); PSA staining may be observed in prostate cancer or normal prostate | DS #1 FIG. 14 |

*The listed color of each stain may be a result of a detection system that may include an anti-mouse antibody perhaps conjugated to HRP and even an anti-rabbit antibody perhaps conjugated to AP, perhaps even with DAB and Fast Red as chromogens, which may result in brown staining for mouse antibodies and red staining for rabbit antibodies (referred to as DS #2). Alternatively, the detection system may include an anti-mouse antibody perhaps conjugated to AP and even an anti-rabbit antibody perhaps conjugated to HRP, perhaps even with DAB and Fast Red as chromogens, which may result in red staining for mouse antibodies and brown staining for rabbit antibodies (referred to as DS #1). In some instances, two colors may not be necessary because the antigens may be distinguished by cellular localization of staining, or perhaps it is not diagnostically significant to determine which antigen is staining. Other color combinations may be obtained using other detection system or chromogens and all are meant to be included in this disclosure.

Figure 6A:
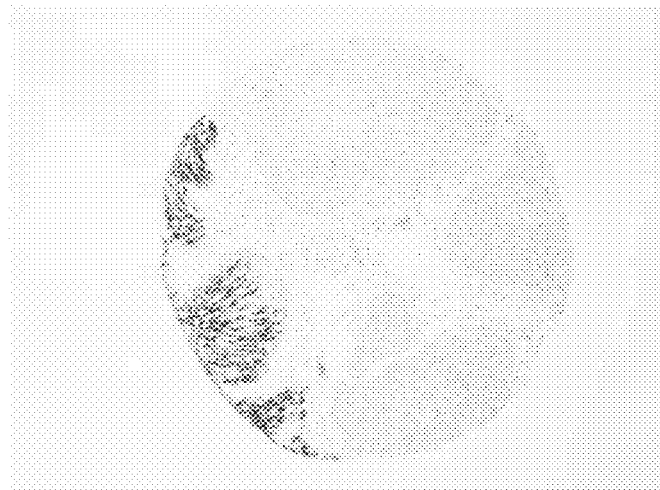
FIG. 6A shows an example of UPIII staining a specimen of urothelial carcinoma. Cytoplasmic and membranous staining of UPIII (brown) is observed.
Figure 6B:
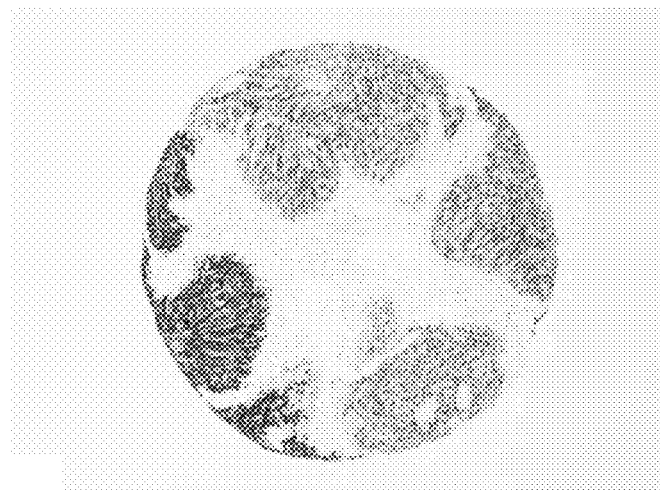
FIG. 6B shows an example of UPII staining the same specimen of urothelial carcinoma as shown in FIG. 6A. Cytoplasmic and membranous staining of UPII (brown) is observed.
Figure 6C:
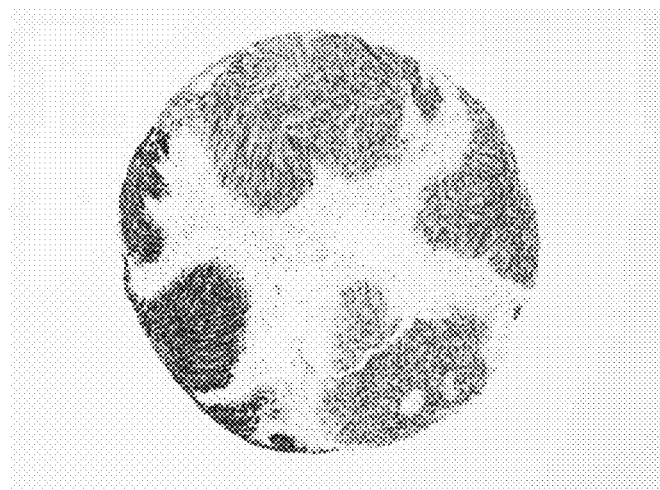
FIG. 6C shows an example of a cocktail of UPIII+UPII staining the same specimen of urothelial carcinoma as shown in FIG. 6A. In this example, brown staining may represent expression of UPII and/or UPIII.
Figure 7A:
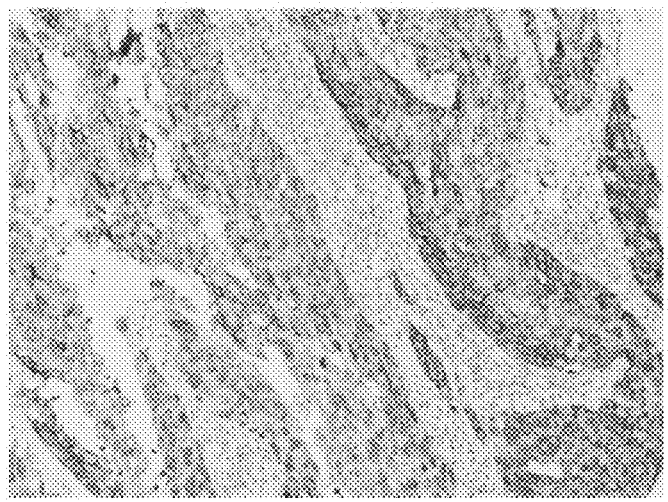
FIG. 7A shows an example of a cocktail of UPIII+p63 staining urothelial carcinoma. Staining of UPIII (brown) is membranous and cytoplasmic. Staining of p63 (nuclear, brown) may be reduced or perhaps absent in this sample.
Figure 7B:
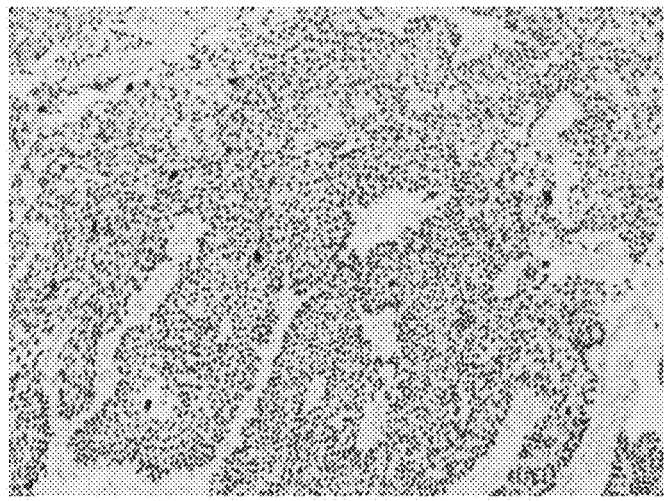
FIG. 7B shows an example of a cocktail of UPIII+p63 staining urothelial carcinoma. Staining of p63 (nuclear, brown) is observed. Staining of UPIII (cytoplasmic and membranous, brown) may be reduced, or perhaps absent in this sample.

In some embodiments, combining UPIII with another antibody that stains urothelial tissue, such as UPII, may be useful, perhaps increasing sensitivity compared to staining with each of the antibodies individually. FIG. 6A shows an example of a cocktail of UPIII+UPII staining a specimen of urothelial carcinoma. The staining of UPIII and UPII individually is shown in FIGS. 6B and 6C, respectively.

Figure 7C:
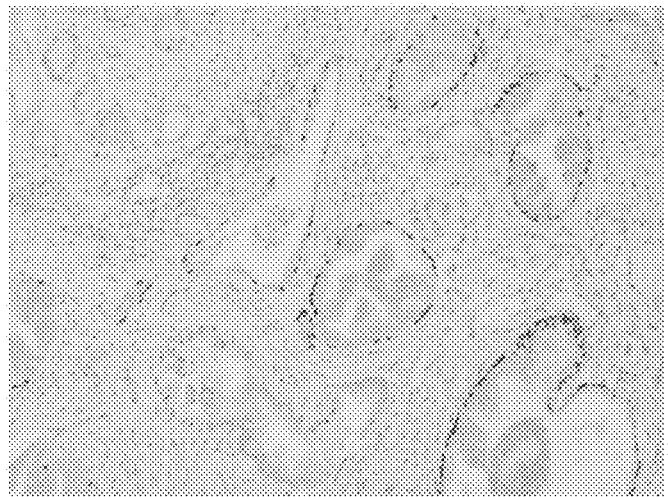
FIG. 7C shows an example of a cocktail of UPIII+p63 staining prostate carcinoma. Staining of p63 (nuclear, brown) is observed as a discontinuous pattern in prostate glands. Staining of UPIII (cytoplasmic and membranous, brown) is absent in this sample.

A cocktail of UPIII+p63 may also be useful in identifying urothelial carcinoma (FIGS. 7A & 7B), perhaps with increased sensitivity compared to UPIII or p63 individually. This cocktail may also be useful in identifying basal cells in prostate glands by p63 staining (FIG. 7C).

Figure 8A:
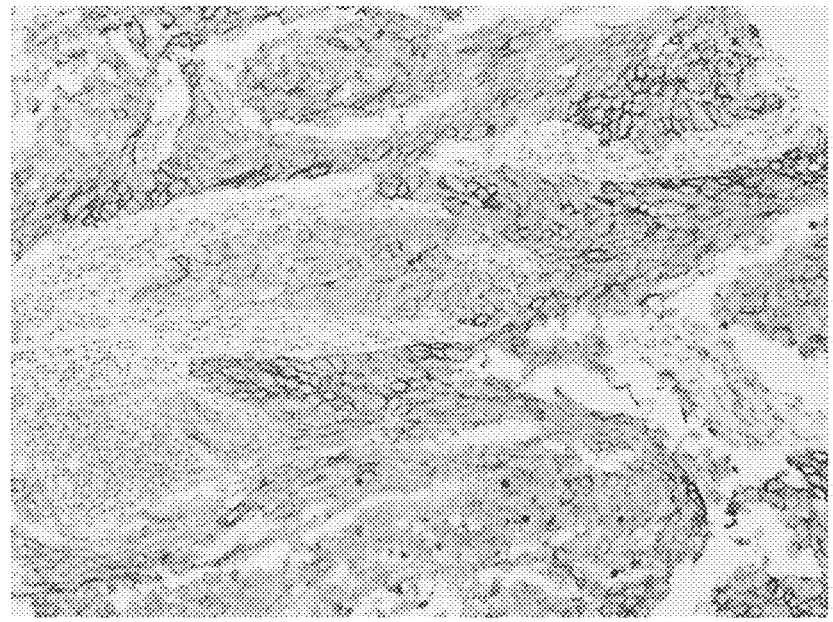
FIG. 8A shows an example of a cocktail of UPIII+PAX8 staining urothelial carcinoma. In this example, staining of UPIII (cytoplasmic and membranous, brown) is observed. No nuclear staining of PAX8 (brown) is observed.
Figure 8B:
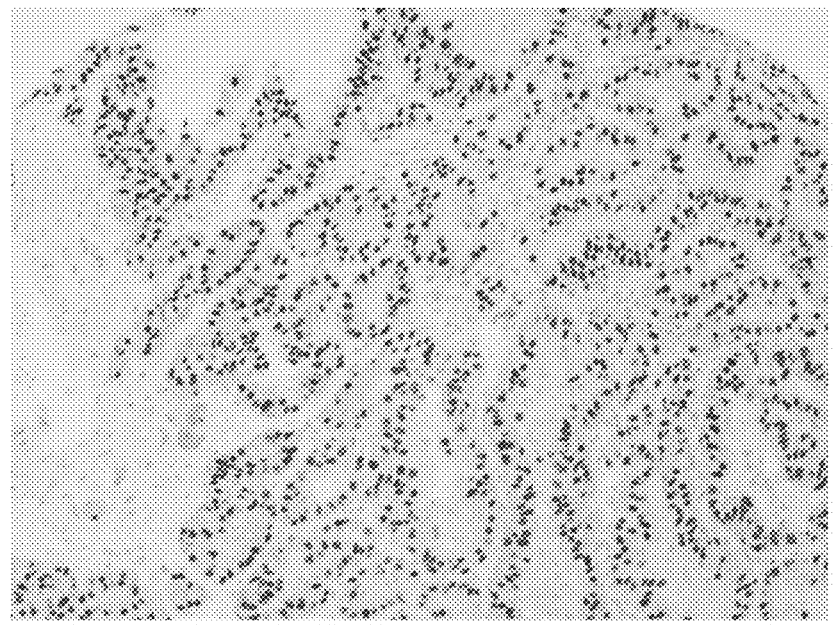
FIG. 8B shows an example of a cocktail of UPIII+PAX8 staining renal cell carcinoma. In this example, staining of PAX8 (brown, nuclear) is observed. No staining of UPIII (cytoplasmic and membranous, brown) is observed.

Combining UPIII+PAX8 may be useful for differentiating urothelial carcinoma and renal cell carcinoma. UPIII may stain urothelial carcinoma, which is not stained by PAX8 (FIG. 8A). In contrast, renal cell carcinoma may be stained by PAX 8, but perhaps not by UPIII (FIG. 8B).

Figure 9C:
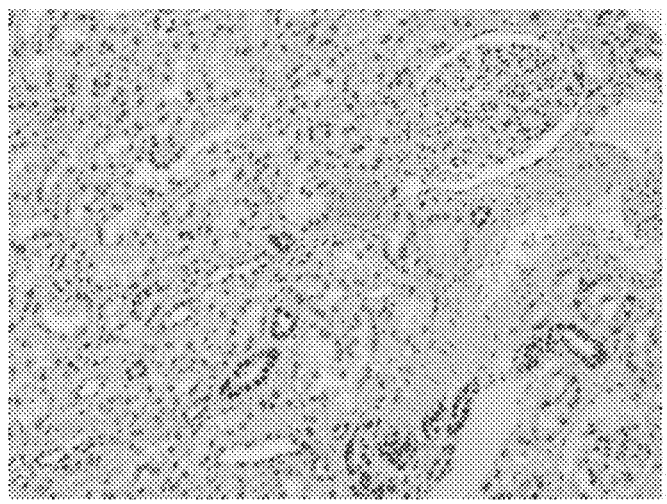
FIG. 9C shows an example of a cocktail of UPIII+ GATA3+PAX8 staining renal cell carcinoma. In this example, staining of PAX8 (red, nuclear) is observed. No staining of UPIII or GATA3 (brown) is observed.

GATA3 may be another antibody useful for staining urothelial tissue. A cocktail of UPIII+GATA3+PAX8 may offer a sensitive marker for urothelial carcinoma that also discriminates renal cell carcinoma. Specimens of urothelial carcinoma may be stained by either UPIII or GATA3, or perhaps both (FIGS. 9A and 9B), but may not stained by PAX8. In contrast, renal cell carcinoma may be identified by staining with PAX8 (FIG. 9C).

Figure 10C:
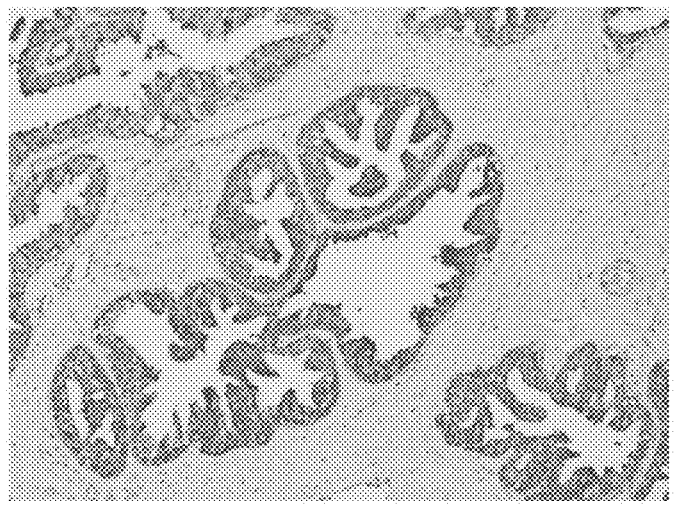
FIG. 10C shows an example of a cocktail of UPIII+ GATA3+PSA staining prostate cancer. Cytoplasmic staining of PSA (red) is observed in prostate glands. No staining of UPIII or GATA 3 (brown) is observed.
Figure 11A:
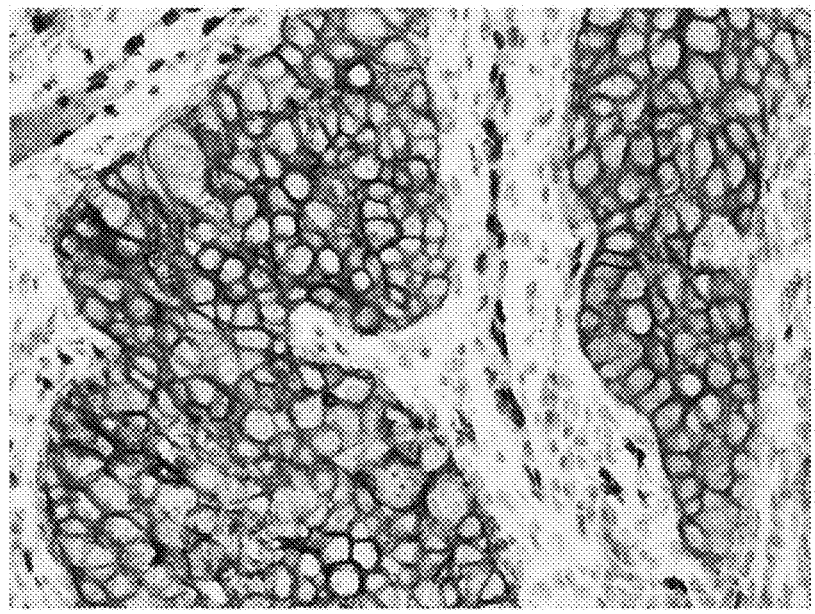
FIG. 11A shows an example of a cocktail of UPIII+ERG staining urothelial carcinoma. Staining of UPIII (brown) is membranous and cytoplasmic. Staining of endothelial cells by ERG (brown) is also shown. No other nuclear staining of ERG is observed.

In some instances it may be useful to discriminate urothelial carcinoma from prostate carcinoma. In these cases, antibodies useful for staining urothelial carcinoma may be combined with antibodies useful for staining prostate carcinoma. For example, a cocktail of UPIII+GATA3+PSA would stain urothelial tissue (UPIII and GATA3) and prostate tissue (PSA). Urothelial carcinoma may stain with UPIII or GATA3 or perhaps both (FIGS. 10A and 10B), but perhaps not be stained by PSA. In contrast, prostate tissue, including prostate carcinoma, may be stained by PSA, but not by UPIII or GATA3 (FIG. 10C).

Figure 11B:
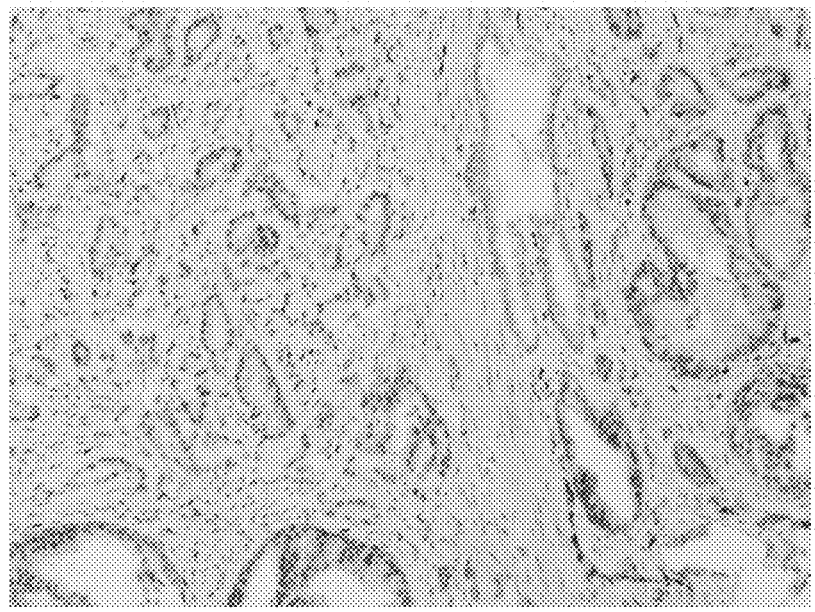
FIG. 11B shows an example of a cocktail of UPIII+ERG staining prostate cancer. Nuclear staining of ERG-positive prostate glands (brown) is shown, as well as ERG staining in endothelial cells. No staining of UPIII is observed.
Figure 12:
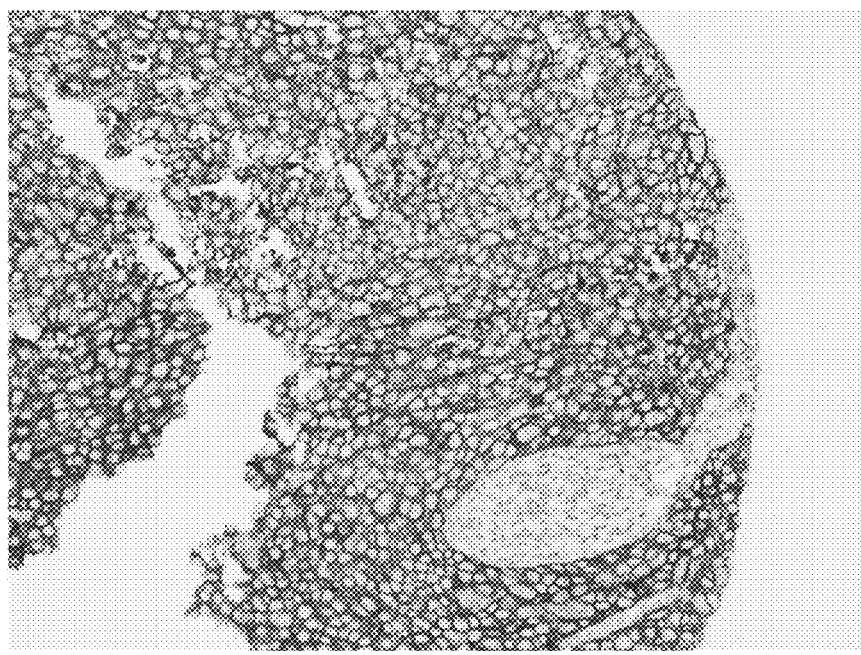
FIG. 12 shows an example of a cocktail of UPIII+ NKX3.1 staining urothelial carcinoma. Staining of UPIII (brown) is membranous and cytoplasmic. No other nuclear staining of NKX3.1 (brown) is observed.
Figure 13A:
FIG. 13A shows an example of a cocktail of UPIII+ERG+ NKX3.1 staining urothelial carcinoma. Staining of UPIII (red) is membranous and cytoplasmic. Staining of endothelial cells by ERG (red) is also shown. No other nuclear staining of ERG or NKX3.1 (brown) is observed.
Figure 13B:
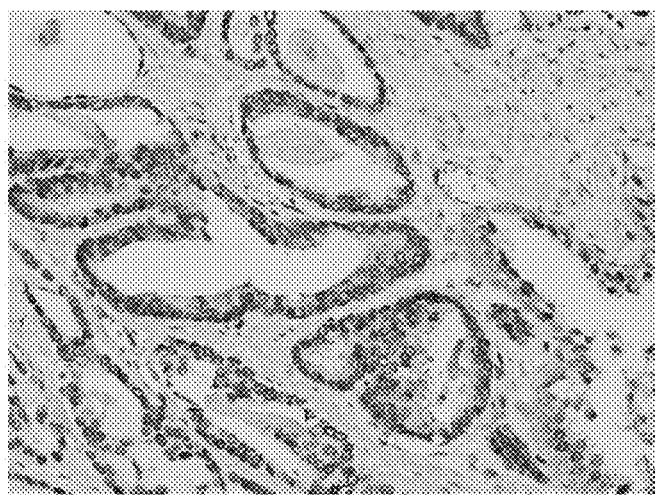
FIG. 13B shows an example of a cocktail of UPIII+ERG+ NKX3.1 staining prostate cancer. Nuclear staining of ERG-positive prostate glands (red) is shown, as well as ERG staining in endothelial cells. Nuclear staining of NKX3.1 (brown) is also observed. No staining of UPIII (brown) is observed.
Figure 13C:
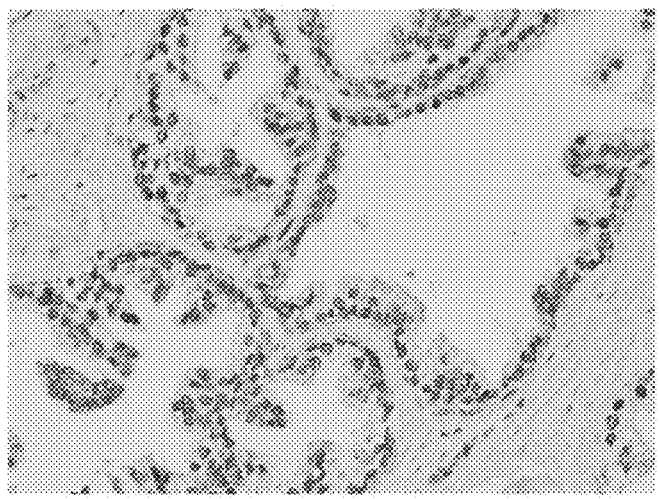
FIG. 13C shows an example of a cocktail of UPIII+ERG+ NKX3.1 staining prostate cancer. ERG staining in endothelial cells (red) is observed without nuclear staining of ERG in prostate glands. Nuclear staining of NKX3.1 (brown) is also observed. No staining of UPIII (brown) is observed.
Figure 14A:
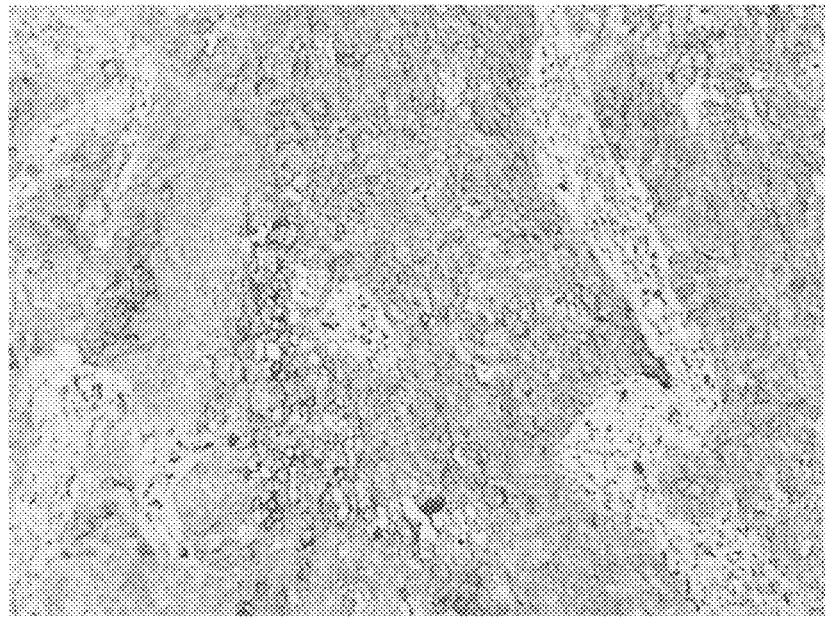
FIG. 14A shows an example of a cocktail of UPIII+ERG+ PSA staining urothelial carcinoma. Staining of UPIII (red) is membranous and cytoplasmic. Staining of endothelial cells by ERG (red) is also shown. No other nuclear staining of ERG or cytoplasmic staining of PSA (brown) is observed.
Figure 14B:
FIG. 14B shows an example of a cocktail of UPIII+ERG+ PSA staining prostate cancer. Cytoplasmic staining of PSA (brown) is observed in prostate glands. ERG staining (red) is observed in endothelial cells. No staining of UPIII (brown) is observed.
Figure 15A:
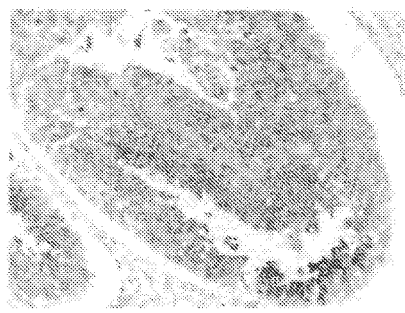
FIG. 15A is a black and white version of FIG. 1A showing an example of BC17 staining on bladder TCC tissue (grade 2).
Figure 15B:
FIG. 15B is a black and white version of FIG. 1B showing an example of AU 1 staining on a serial section of the same bladder TCC tissue of FIG. 1A.
Figure 16A:
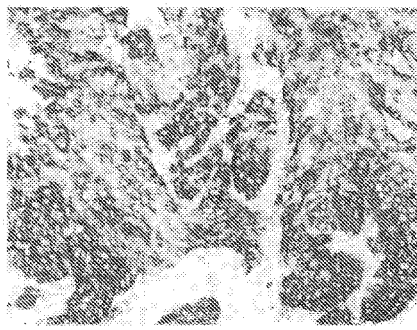
FIG. 16A is a black and white version of FIG. 2A showing an example of BC17 staining on bladder TCC tissue (grade 2).
Figure 16B:
FIG. 16B is a black and white version of FIG. 2B showing an example of AU 1 staining on a serial section of the same bladder TCC tissue of FIG. 2A.
Figure 17A:
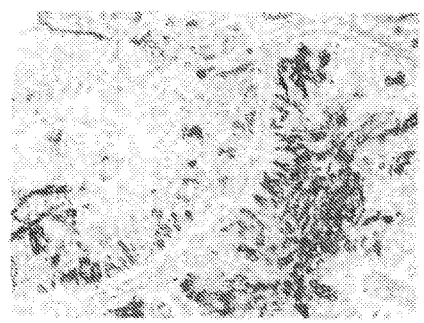
FIG. 17A is a black and white version of FIG. 3A showing an example of BC17 staining on bladder TCC tissue (grade 2).
Figure 17B:
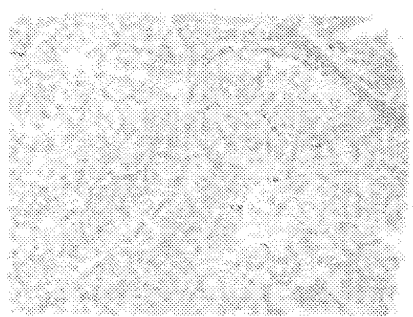
FIG. 17B is a black and white version of FIG. 3B showing an example of AU 1 staining on a serial section of the same bladder TCC tissue of FIG. 3A.
Figure 18A:
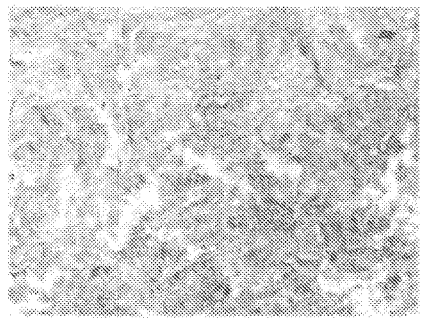
FIG. 18A is a black and white version of FIG. 4A showing an example of BC17 staining on bladder TCC tissue (grade 3).
Figure 18B:
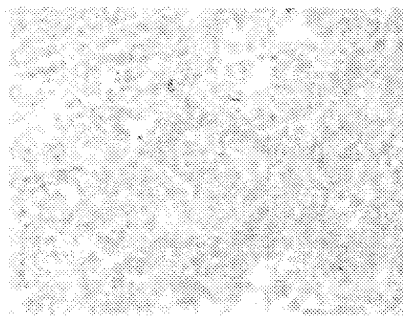
FIG. 18B is a black and white version of FIG. 4B showing an example of AU 1 staining on a serial section of the same bladder TCC tissue of FIG. 4A.
Figure 19:
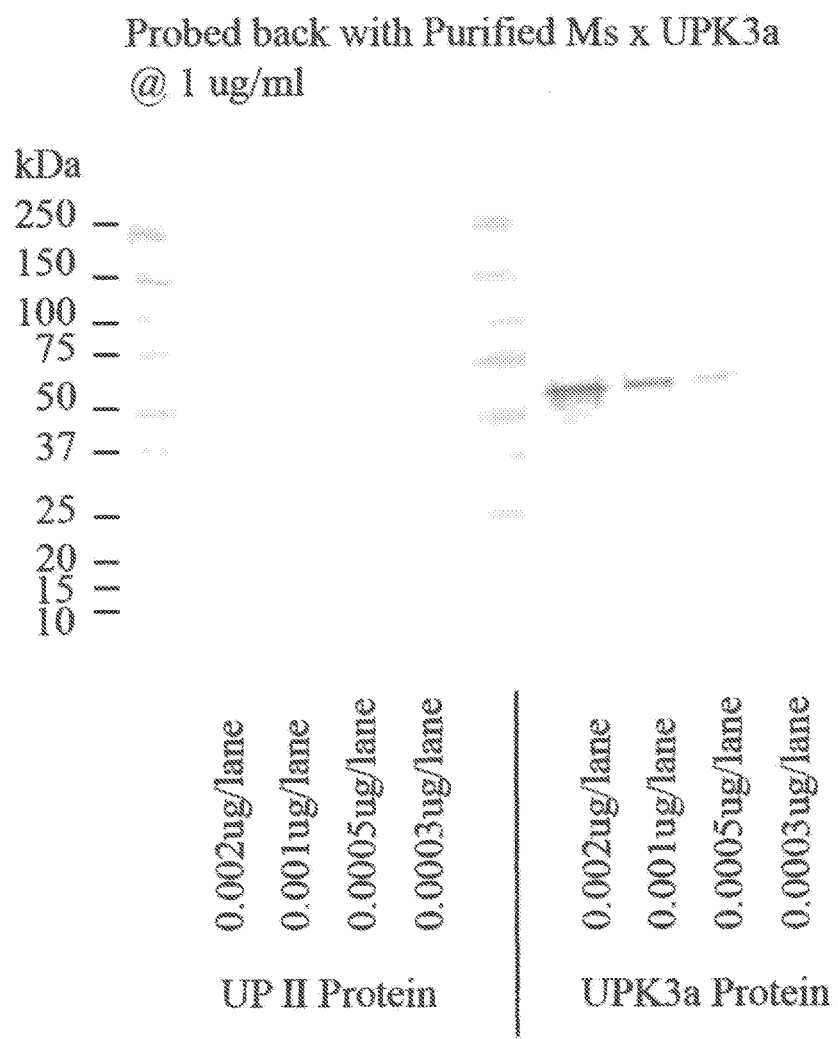
FIG. 19 is a black and white version of FIG. 5 showing a Western Blot of anti-UPIII antibody BC17 with Uroplakin II protein (left lanes) and Uroplakin III protein (right lanes).
Figure 20A:
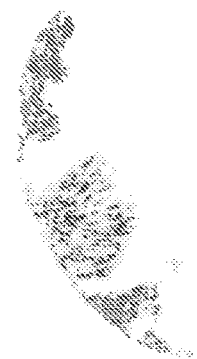
FIG. 20A is a black and white version of FIG. 6A showing an example of UPIII staining a specimen of urothelial carcinoma. Cytoplasmic and membranous staining of UPIII is observed.
Figure 20B:
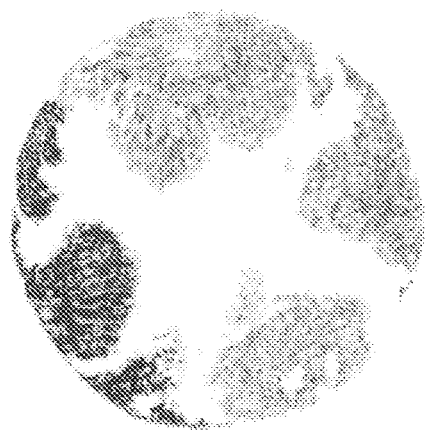
FIG. 20B is a black and white version of FIG. 6B showing an example of UPII staining the same specimen of urothelial carcinoma as shown in FIG. 6A. Cytoplasmic and membranous staining of UPII is observed.
Figure 20C:
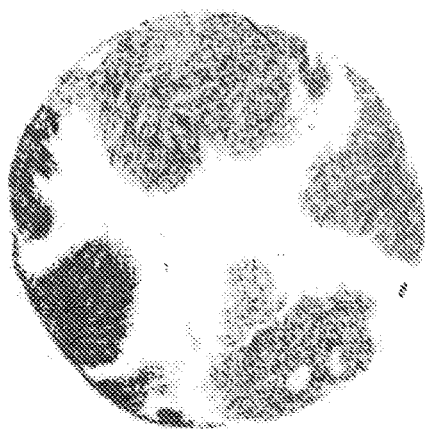
FIG. 20C is a black and white version of FIG. 6C showing an example of a cocktail of UPIII+UPII staining the same specimen of urothelial carcinoma as shown in FIG. 6A. In this example, staining may represent expression of UPII and/or UPIII.
Figure 21A:
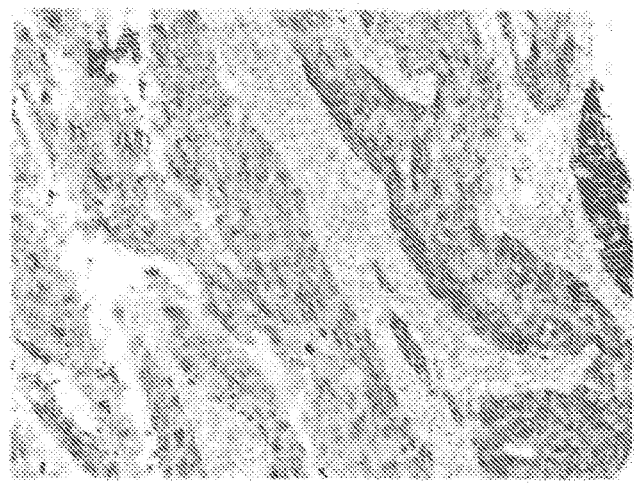
FIG. 21A is a black and white version of FIG. 7A showing an example of a cocktail of UPIII+p63 staining urothelial carcinoma. Staining of UPIII is membranous and cytoplasmic. Staining of p63 (nuclear) may be reduced or perhaps absent in this sample.
Figure 21B:
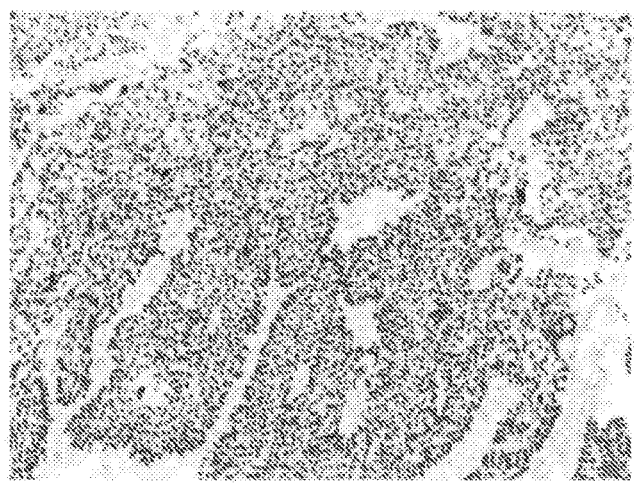
FIG. 21B is a black and white version of FIG. 7B showing an example of a cocktail of UPIII+p63 staining urothelial carcinoma. Staining of p63 (nuclear) is observed. Staining of UPIII (cytoplasmic and membranous) may be reduced, or perhaps absent in this sample.
Figure 21C:
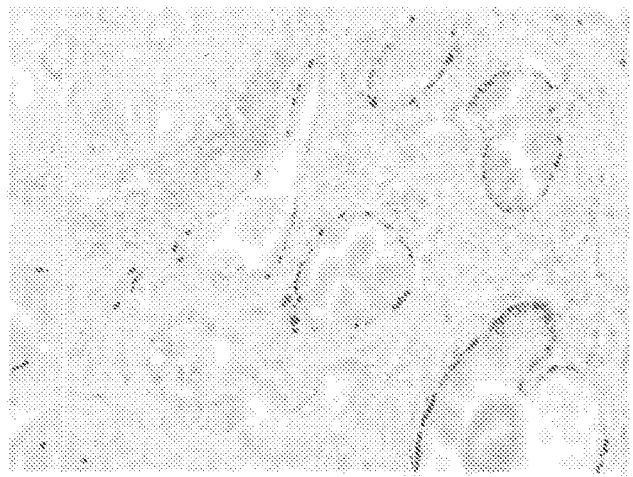
FIG. 21C is a black and white version of FIG. 7C showing an example of a cocktail of UPIII+p63 staining prostate carcinoma. Staining of p63 (nuclear) is observed as a discontinuous pattern in prostate glands. Staining of UPIII (cytoplasmic and membranous) is absent in this sample.
Figure 22A:
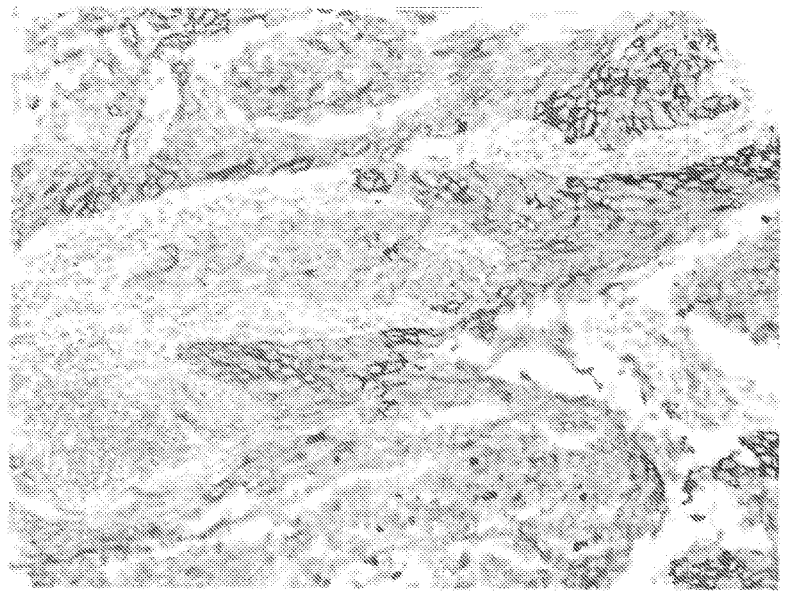
FIG. 22A is a black and white version of FIG. 8A showing an example of a cocktail of UPIII+PAX8 staining urothelial carcinoma. In this example, staining of UPIII (cytoplasmic and membranous) is observed. No nuclear staining of PAX8 is observed.
Figure 22B:
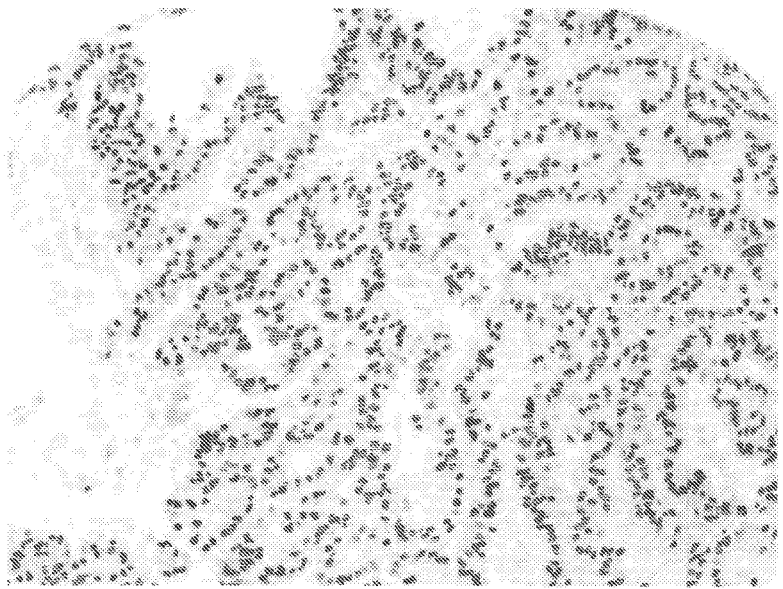
FIG. 22B is a black and white version of FIG. 8B showing an example of a cocktail of UPIII+PAX8 staining renal cell carcinoma. In this example, staining of PAX8 (nuclear) is observed. No staining of UPIII (cytoplasmic and membranous) is observed.
Figure 23A:
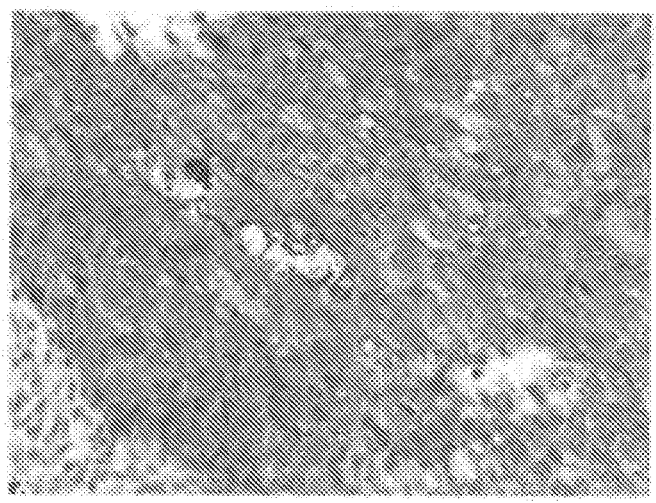
FIG. 23A is a black and white version of FIG. 9A showing an example of a cocktail of UPIII+GATA3+PAX8 staining urothelial carcinoma. In this example, staining of both UPIII (membranous & cytoplasmic) and GATA3 (nuclear) is observed. No staining of PAX8 is observed.
Figure 23B:
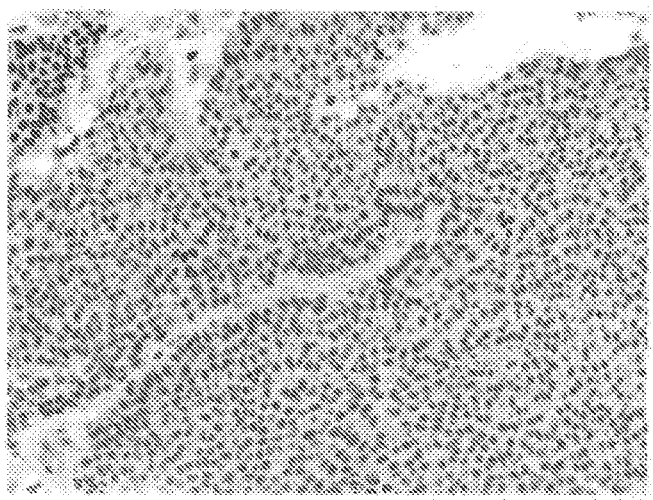
FIG. 23B is a black and white version of FIG. 9B showing an example of a cocktail of UPIII+GATA3+PAX8 staining urothelial carcinoma. In this example, staining of GATA3 (nuclear) observed. No staining of PAX8 is observed.
Figure 23C:
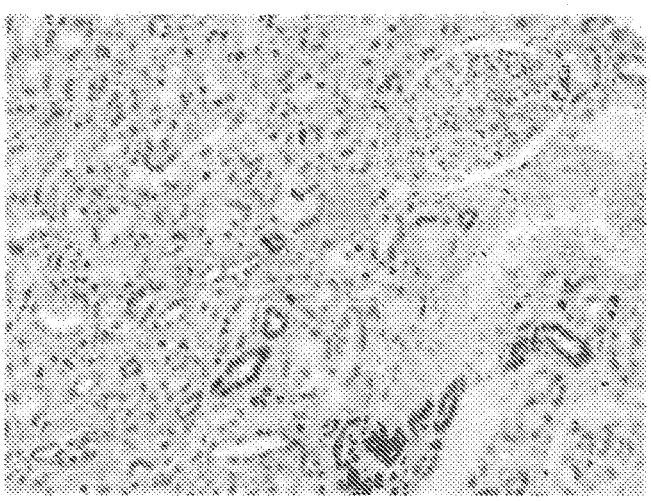
FIG. 23C is a black and white version of FIG. 9C showing an example of a cocktail of UPIII+GATA3+PAX8 staining renal cell carcinoma. In this example, staining of PAX8 (nuclear) is observed. No staining of UPIII or GATA3 is observed.
Figure 24A:
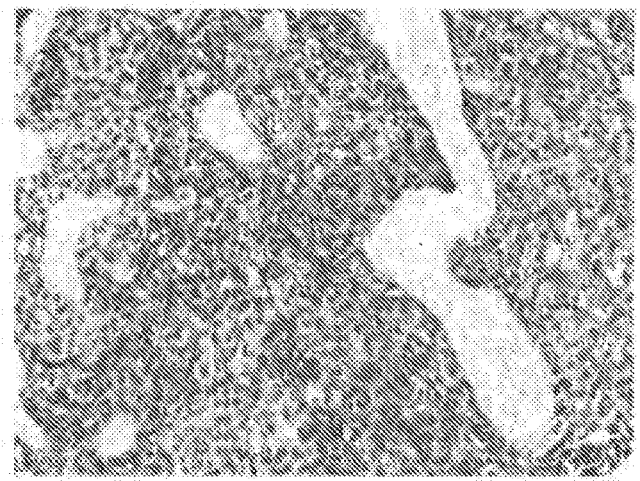
FIG. 24A is a black and white version of FIG. 10A showing an example of a cocktail of UPIII+GATA3+PSA staining urothelial carcinoma. Staining of UPIII is membranous and cytoplasmic and staining of GATA3 is nuclear. No other cytoplasmic staining of PSA is observed.
Figure 24B:
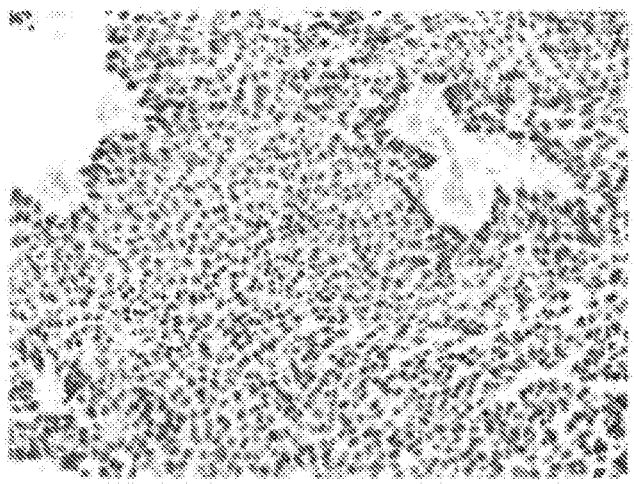
FIG. 24B is a black and white version of FIG. 10B showing an example of a cocktail of UPIII+GATA3+PSA staining urothelial carcinoma. Staining GATA3 is nuclear. No other nuclear staining of UPIII or cytoplasmic staining of PSA is observed.
Figure 24C:
FIG. 24C is a black and white version of FIG. 10C showing an example of a cocktail of UPIII+GATA3+PSA staining prostate cancer. Cytoplasmic staining of PSA is observed in prostate glands. No staining of UPIII or GATA 3 is observed.
Figure 25A:
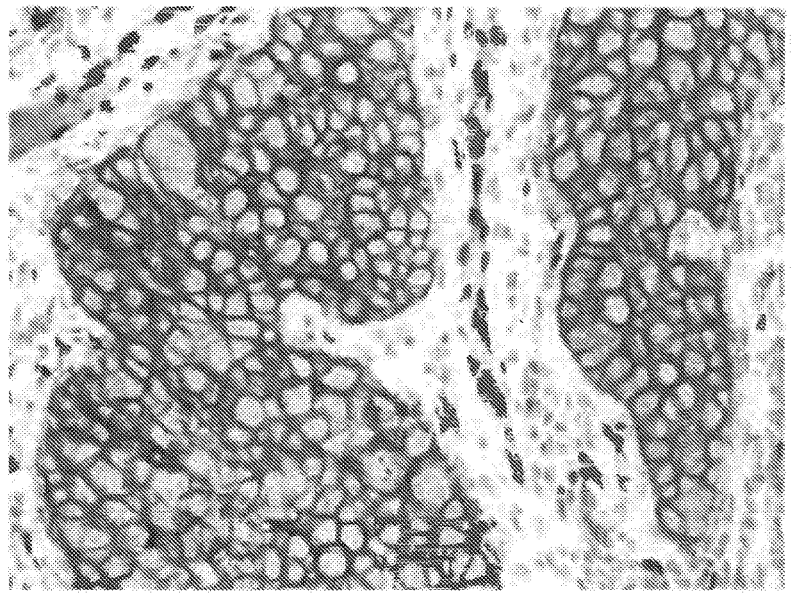
FIG. 25A is a black and white version of FIG. 11A showing an example of a cocktail of UPIII+ERG staining urothelial carcinoma. Staining of UPIII is membranous and cytoplasmic. Staining of endothelial cells by ERG is also shown. No other nuclear staining of ERG is observed.
Figure 25B:
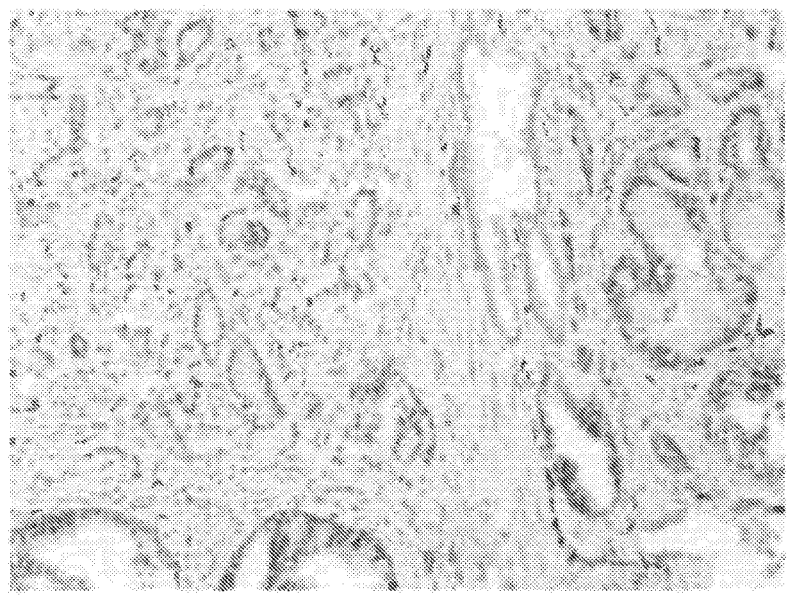
FIG. 25B is a black and white version of FIG. 11B showing an example of a cocktail of UPIII+ERG staining prostate cancer. Nuclear staining of ERG-positive prostate glands is shown, as well as ERG staining in endothelial cells. No staining of UPIII is observed.
Figure 26:
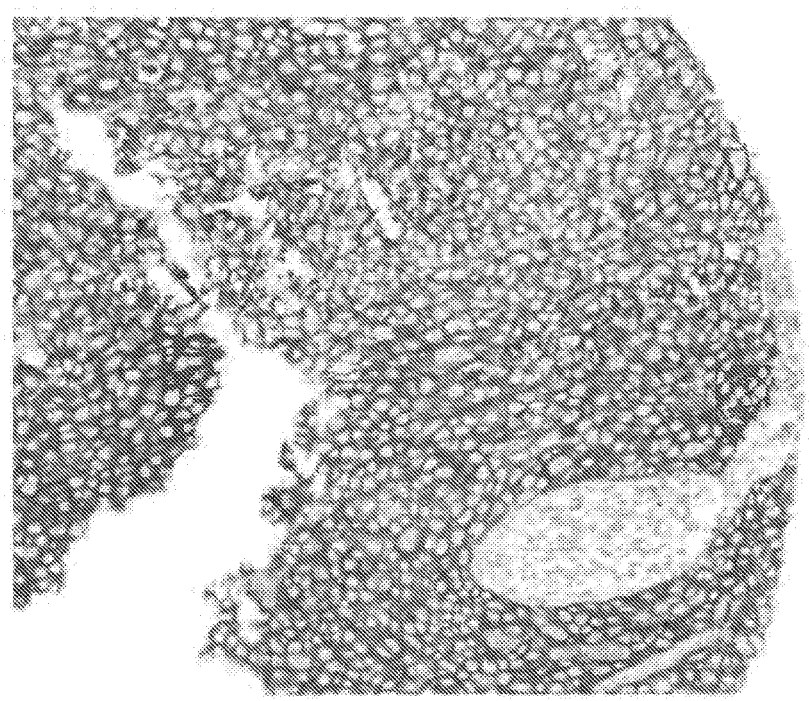
FIG. 26 is a black and white version of FIG. 12 showing an example of a cocktail of UPIII+NKX3.1 staining urothelial carcinoma. Staining of UPIII is membranous and cytoplasmic. No other nuclear staining of NKX3.1 is observed.
Figure 27A:
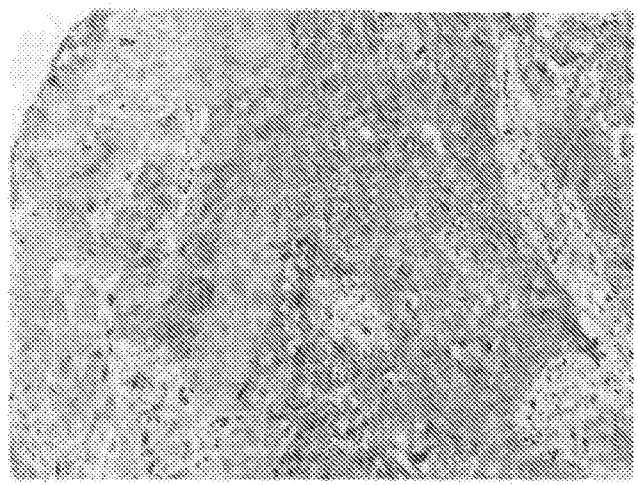
FIG. 27A is a black and white version of FIG. 13A showing an example of a cocktail of UPIII+ERG+NKX3.1 staining urothelial carcinoma. Staining of UPIII is membranous and cytoplasmic. Staining of endothelial cells by ERG is also shown. No other nuclear staining of ERG or NKX3.1 is observed.
Figure 27B:
FIG. 27B is a black and white version of FIG. 13B showing an example of a cocktail of UPIII+ERG+NKX3.1 staining prostate cancer. Nuclear staining of ERG-positive prostate glands is shown, as well as ERG staining in endothelial cells. Nuclear staining of NKX3.1 is also observed. No staining of UPIII is observed.
Figure 27C:
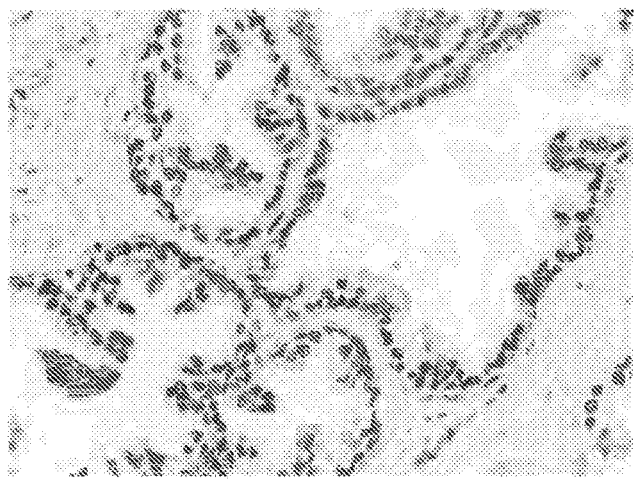
FIG. 27C is a black and white version of FIG. 13C showing an example of a cocktail of UPIII+ERG+NKX3.1 staining prostate cancer. ERG staining in endothelial cells is observed without nuclear staining of ERG in prostate glands. Nuclear staining of NKX3.1 is also observed. No staining of UPIII is observed.
Figure 28A:
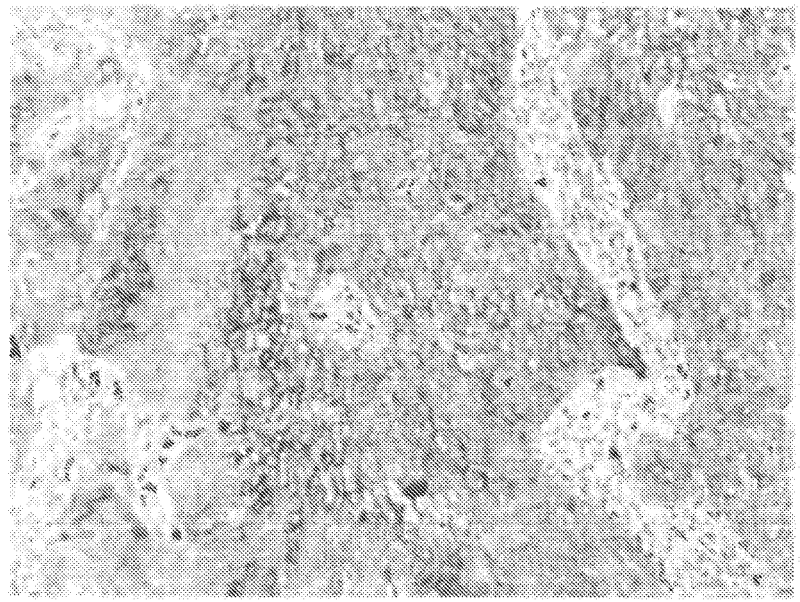
FIG. 28A is a black and white version of FIG. 14A showing an example of a cocktail of UPIII+ERG+PSA staining urothelial carcinoma. Staining of UPIII is membranous and cytoplasmic. Staining of endothelial cells by ERG is also shown. No other nuclear staining of ERG or cytoplasmic staining of PSA is observed.
Figure 28B:
FIG. 28B is a black and white version of FIG. 14B showing an example of a cocktail of UPIII+ERG+PSA staining prostate cancer. Cytoplasmic staining of PSA is observed in prostate glands. ERG staining is observed in endothelial cells. No staining of UPIII is observed.

Other antibodies for prostate tissue may also be useful when combined with UPIII. For example, a cocktail of UPIII+ERG may be useful for discriminating urothelial carcinoma from prostate carcinoma. UPIII may stain urothelial carcinoma (FIG. 11A), but ERG may only stain endothelial cells in this tissue. In prostate carcinoma, staining of ERG may be observed in prostate glands and endothelial cells, but no staining of UPIII may be observed (FIG. 11B). In another example, a cocktail of UPIII+NKX3.1 may be useful for discriminating urothelial carcinoma from prostate carcinoma. With this cocktail, UPIII may stain urothelial carcinoma (FIG. 12), but NKX3.1 may not stain this tissue. In a further example, both ERG and NKX3.1 may be combined with UPIII in a cocktail (UPIII+ERG+NKX3.1). With this cocktail, urothelial carcinoma may be stained by UPIII, but not ERG or NKX3.1 (FIG. 13A). Prostate carcinoma may be stained by ERG or NKX3.1, or perhaps both, but not stained by UPIII (FIGS. 13B and 13C). In another example useful for discriminating urothelial carcinoma from prostate carcinoma, a cocktail of UPIII+ERG+PSA may be used. In this example, urothelial carcinoma may stain with UPIII, but not with ERG or PSA (FIG. 14A). Prostate carcinoma may stain with PSA or ERG, or perhaps both, but not stain with UPIII (FIG. 14B).

The mouse monoclonal UP III antibody BC17 may be specific for detection of UP III and may be useful in immunohistochemical procedures for diagnosis of several types of cancers in human tissue samples. In particular, BC17 has advantages over previously known UP III antibodies, including greater sensitivity.

In embodiments, BC17 may also be useful in the identification of UPIII expressing cells in other biological specimens, including, but not limited to, blood, urine, or the like. For these specimens, BC17 may be used in an ELISA or other immunocytochemistry technique, perhaps using methods that may be well known to those in the art. In the case of Uroplakin II, RT-PCR of mRNA extracted from the peripheral blood of patients was shown to be a sensitive and specific assay for detecting urothelial carcinoma (see Li S M et. al., *J Urol,* 1999; 162:931-935, hereby incorporated by reference herein). In an analogous manner, detection of Uroplakin III protein from the circulating cells of peripheral blood may be a sensitive and/or specific assay for the detection of urothelial carcinoma, which may be particularly useful for monitoring for recurrence, or metastasis, in patients previously diagnosed with urothelial carcinoma.

Determination of Uroplakin III protein in patient urine may be a potentially sensitive marker for urothelial carcinoma (see Lai Y et. al., *Urology,* 2010; 76:514.e6-11, hereby incorporated by reference herein). BC17 may be used in a similar assay (perhaps replacing AU1) to identify Uroplakin III protein in urine specimens using ELISA. Immunocytochemistry may also be a common diagnostic method for specimens such as urine. BC17 may be used in immunocytochemistry to identify Uroplakin III containing cells, which may aid in the diagnosis or monitoring of urothelial carcinoma. Cytology, and immunocytochemistry in particular, may be well known in the art. For example, MCM-2 protein may be identified in urine specimens by immunocytochemistry, using an anti-MCM-2 antibody (see Saeb-Parsy K et. al. *Br J Cancer,* 2012; 107:1384-1391, hereby incorporated by reference herein). In the same manner, the anti-Uroplakin III antibody BC17 may be used in immunocytochemical assays of urine to identify Uroplakin III protein.

Determination of Uroplakin III levels may be a useful prognostic factor and indicator of patient outcomes. Loss of Uroplakin III expression, as determined by IHC, has been associated with aggressive bladder cancer and shown to be predictive of patient survival (see Matsumoto K et. al. *Urology,* 2008; 72:444-449, and Ohtsuka Y et. al. *BJU Int,* 2006; 97:1322-1326, hereby incorporated by reference herein). As such, the various systems and methods as discussed herein may provide a detection system such as but not limited to detection of cancer, diagnose or even prognose cancer, predict an outcome of cancer, assess efficacy of treatment of cancer, predict recurrence of cancer, or the like. As mentioned herein, use of an antibody or fragment thereof may be performed on an automated staining device. Detection may be made automatically, manually, by image analysis, or the like. Detection may utilize a method including but not limited to immunohistochemistry (IHC), IHC of FFPE, IHC of frozen-tissue sections, immunocytochemistry, ELISA, or the like.

Figure 30:
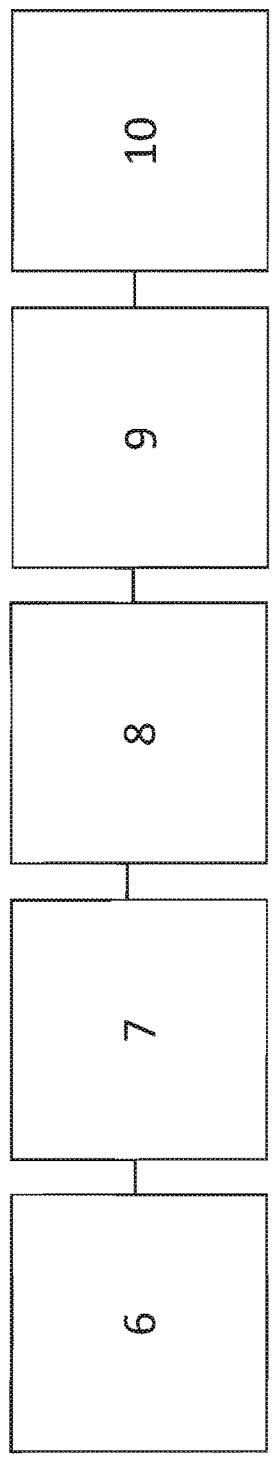
FIG. 30 shows an example schematic of an immunoassay method in accordance with various embodiments of the present invention, including obtaining tissue from an animal or human to be tested (6), fixing or freezing said tissue (7), treating said fixed or frozen tissue to unmask epitopes to Uroplakin III (8), contacting the treated tissue with an antibody or fragment thereof that binds to Uroplakin III protein if the protein is present in said tissue (9), and even detecting the presences of said bound antibodies (10).

As but one example of an immunoassay method, embodiments of the present invention may provide obtaining tissue from an animal or human to be tested (6), fixing or freezing said tissue (7), treating said fixed or frozen tissue to unmask epitopes to Uroplakin III (8), contacting said treated tissue with an antibody or fragment thereof as discussed herein in an amount and under conditions such that an antibody or fragment thereof binds to a Uroplakin III protein if the protein is present in said tissue (9); and perhaps even detecting the presences of said bound antibodies (10), as schematically represented in FIG. 30.

Figure 29:
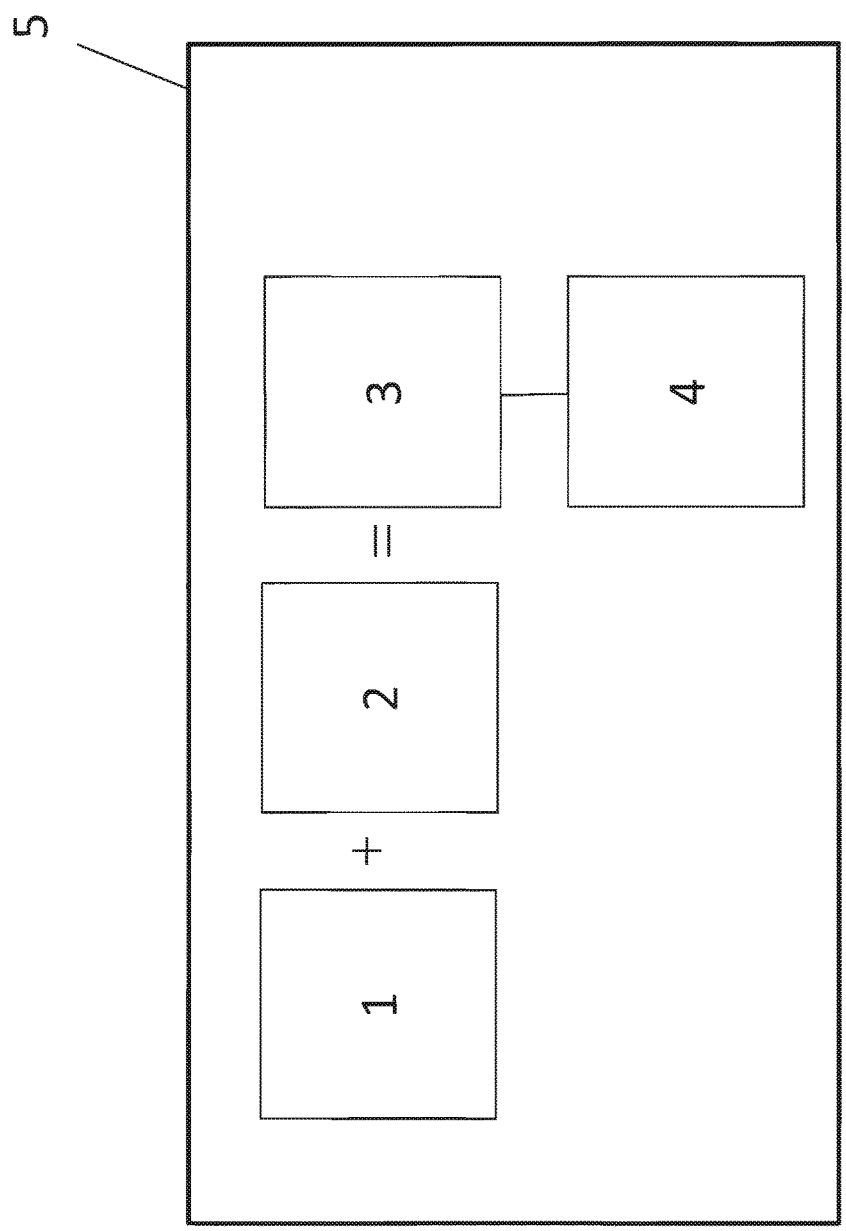
FIG. 29 shows a schematic of a kit in accordance with various embodiments of the present invention. A kit (5) may provide an antibody (1), fragment thereof, portion thereof, in a composition or even in a cocktail, perhaps even provided from a hybridoma, the antibody (1) or the like may be contacted with a biological sample (2) to form at least one antibody-antigen complex (3) which may then be detected with a detector (4).

FIG. 29 shows a schematic summary of various embodiments of the present invention including a kit (5) which may provide an antibody, fragment thereof, portion thereof, in a composition or even in a cocktail, perhaps even provided from a hybridoma, the antibody (1) or the like may be contacted with a biological sample (2) to form at least one antibody-antigen complex (3) which may then be detected with a detector (4).

The present invention may provide, in embodiments, a diagnostic or even prognostic test kit which may include an antibody or fragment thereof (as discussed herein) with an antibody detection element of the antibody or fragment thereof perhaps when bound to an antigen. This may provide a method of contacting a biological sample with an antibody or fragment thereof and even detecting binding of, or even the presence of the antibody or fragment thereof bound to a protein or with an antigen in the biological sample perhaps using an antibody detection element. Embodiments may provide an immunoassay method for detecting Uroplakin III protein in a mammal or human perhaps by obtaining a tissue from an animal or a human to be tested, contacting the tissue with an antibody or fragment thereof in accordance with the various embodiments presented herein perhaps in an amount and under conditions such that the antibody or fragment thereof may bind to a Uroplakin III protein if the protein is present in the tissue; and even detecting the presence of bound antibodies. A biological sample may include but is not limited to blood, urine, urothelial tissue, transitional cell tissue, bladder tissue, normal tissue, neoplastic tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, prostate tissue, lung tissue, breast tissue, or the like perhaps depending on the antibody or even cocktail being used.

It is noted that use of terms such as UPIII, UPIII antibody, BC17, or the like may relate to anti-UPIII antibodies or the like as appropriate as one skilled in the art would understand.

As can be easily understood from the foregoing, the basic concepts of the present invention may be embodied in a variety of ways. It involves both antibody techniques as well as devices to accomplish the appropriate antibody. In this application, the antibody techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detection" or "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any law, statutes, regulations, or rules mentioned in this application for patent; or patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the antibody devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group*, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 2 or any other claim" or the like, it could be re-drafted as dependent on claim 1, claim 3, or even claim 4 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The invention claimed is:

1. An isolated antibody produced by the hybridoma deposited with the American Type Culture Collection (ATCC) under ATCC Patent Deposit Designation No. PTA-12699 or an isolated antigen binding fragment of said isolated antibody, wherein said isolated antibody and antigen binding fragment thereof specifically bind to Uroplakin III comprising SEQ ID NO: 3, and wherein said isolated antibody and isolated antigen binding fragment thereof both comprise six parental CDRs.

2. A composition comprising said isolated antibody or antigen binding fragment thereof of claim 1 and at least one additional isolated antibody or an isolated antigen binding fragment thereof, wherein each additional isolated antibody and said isolated antigen binding fragment thereof are for cancer detection.

3. A cancer diagnostic agent which comprises an antibody or antigen binding fragment thereof according to claim 1 conjugated with a label.

4. A composition comprising said isolated antibody or antigen binding fragment thereof of claim 1 and at least two additional isolated antibodies or isolated antigen binding fragment thereof, wherein each additional isolated antibody and said isolated antigen binding fragments thereof are for cancer detection.

* * * * *

SEQUENCE LISTING

```
<160> NUMBER OF SEQ ID NOS: 3

<210> SEQ ID NO 1
<211> LENGTH: 336
<212> TYPE: DNA
<213> ORGANISM: Mus musculus

<400> SEQUENCE: 1
cagatccagt tggtgcagtc tggacctgag ctgaagaagc ctggagagac agtcaagatc      60
tcctgcaagg cttctggtta taccttcaca gactattcaa tacactgggt gaagcaggct     120
ccaggaaagg gtttaaagtg gacgggctgg ataaacactg agactggtga gccaacatat     180
gcagatgact tcaagggacg gtttgccttc tctttggaaa cctctgccag cactgcctat     240
ttgcagatca acaacctcaa aaatgaggac acggctacat atttctgtgc tagtgggget     300 gtctggggcc aagggactct ggtcgctgtc tctgca                                336

<210> SEQ ID NO 2
<211> LENGTH: 316
```

```
<212> TYPE: DNA
<213> ORGANISM: Mus musculus

<400> SEQUENCE: 2
caaattgttc tcacccagtc tccagcaatc atgtctgcat ctctagggga ggagattacc      60
ctaacctgca gtgccagctc gagtgtaagt tacatgcact ggtaccagca gaagtcaggc     120
acttctccca aactcttgat ttatagcaca tccaacctgg cttctggagt cccttctcgc     180
ttcagtggca gtgggtctgg gacctttttat tctctcacaa tcactagtgt ggaggctaaa   240
gatgctgccg attattactg ccatcagtgg agttgttatc ggacgttcgg tggaggcacc    300
aagcaggaaa tcaaac                                                    316

<210> SEQ ID NO 3
<211> LENGTH: 9
<212> TYPE: PRT
<213> ORGANISM: Homo sapiens

<400> SEQUENCE: 3

Ser Leu Pro Phe Phe Leu Leu Val Gly
1               5
```